United States Patent
Bastian et al.

(10) Patent No.: US 11,117,902 B2
(45) Date of Patent: *Sep. 14, 2021

(54) SELECTIVE ESTROGEN RECEPTOR DEGRADERS

(71) Applicant: Eli Lilly and Company, Indianapolis, IN (US)

(72) Inventors: Jolie Anne Bastian, Indianapolis, IN (US); Jeffrey Daniel Cohen, Indianapolis, IN (US); Almudena Rubio, Carmel, IN (US); Daniel Jon Sall, Greenwood, IN (US); Jennifer Anne McMahon, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/876,819

(22) Filed: May 18, 2020

(65) Prior Publication Data
US 2020/0347073 A1 Nov. 5, 2020

Related U.S. Application Data

(63) Continuation of application No. 16/508,745, filed on Jul. 11, 2019, now Pat. No. 10,654,866.

(60) Provisional application No. 62/697,100, filed on Jul. 12, 2018.

(51) Int. Cl.
*C07D 491/052* (2006.01)
*A61P 35/00* (2006.01)
*A61K 45/06* (2006.01)

(52) U.S. Cl.
CPC .......... *C07D 491/052* (2013.01); *A61P 35/00* (2018.01); *A61K 45/06* (2013.01)

(58) Field of Classification Search
CPC ...... C07D 491/052; A61P 35/00; A61K 45/00
See application file for complete search history.

(56) References Cited

U.S. PATENT DOCUMENTS

| | | | |
|---|---|---|---|
| 8,217,032 B2 | 7/2012 | Dally et al. | |
| 9,845,291 B2 | 12/2017 | Liang et al. | |
| 10,654,866 B2 * | 5/2020 | Bastian | C07D 491/052 |

FOREIGN PATENT DOCUMENTS

WO WO/2018/108954 A1 6/2018

OTHER PUBLICATIONS

Xaio, Bioorg & Med Chem Lett, VOi 11, 2875-2878, 2001. (Year: 2001).
Yao, ACS Catalysis, vol. 6, 1024-1027, 2016. (Year: 2016).
Huang, PLOS One, VOi 9(2), e87897, p. 1-9, 2014. (Year: 2014).

* cited by examiner

*Primary Examiner* — D Margaret M Seaman
(74) *Attorney, Agent, or Firm* — Bradley W Crawford

(57) ABSTRACT

Novel selective estrogen receptor degraders (SERDs) according to the formula:

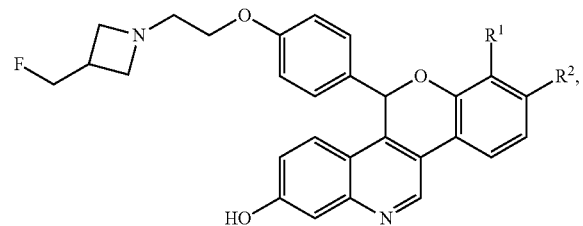

pharmaceutically acceptable salts thereof, and pharmaceutical compositions thereof, wherein either $R^1$ or $R^2$ is independently selected from Cl, F, —$CF_3$, or —$CH_3$, and the other is hydrogen, and methods for their use are provided.

16 Claims, No Drawings

SELECTIVE ESTROGEN RECEPTOR DEGRADERS

This application claims the benefit of U.S. Provisional Application No. 62/697,100, filed Jul. 12, 2018.

BACKGROUND

Selective estrogen receptor degraders (SERDs) bind to the estrogen receptor (ER) and downregulate ER-mediated transcriptional activity. This degradation and downregulation caused by SERDs can be useful in the treatment of cell proliferation disorders, such as cancer. Some small molecule examples of SERDs have been disclosed in the literature (see, e.g., WO2005073204, WO2014205136, and WO2016097071). However, known SERDs have not yet been as useful as is needed to effectively treat cancer. For example, finding SERDs with better pharmacokinetic (PK) and pharmacodynamic (PD) properties, higher efficiency in the clinic, and good oral bioavailability would be very helpful in treating cancer. A pure antagonist SERD with potent inhibition of ER-mediated transcription would be expressly beneficial in treating cancer. There is a need for new SERDs to treat cancers such as breast cancer, ovarian cancer, endometrial cancer, prostate cancer, uterine cancer, gastric cancer, and lung cancer as well as mutations due to emerging resistance. In particular there is a need for new SERDs to treat ER-positive breast cancer, gastric cancer, and/or lung cancer.

SUMMARY

Compounds of the Formula:

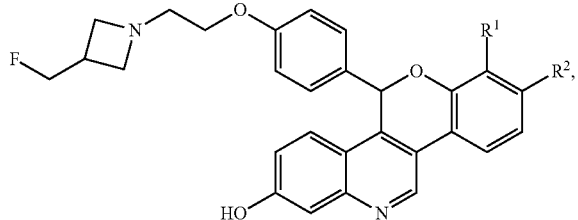

and pharmaceutically acceptable salts thereof, and pharmaceutical compositions thereof, are provided herein. In this formula either $R^1$ or $R^2$ is independently selected from Cl, F, —$CF_3$, or —$CH_3$, and the other is hydrogen.

Methods of using the compounds as described herein, pharmaceutically acceptable salts thereof, and pharmaceutical compositions thereof, to treat breast cancer, ovarian cancer, endometrial cancer, prostate cancer, uterine cancer, gastric cancer, or lung cancer are also provided. The methods include administering a therapeutically effective amount of a compound as described herein, or a pharmaceutically acceptable salt thereof, to a patient in need.

Further provided are the compound as described herein, and a pharmaceutically acceptable salts thereof, for use in therapy. The compounds described herein, and pharmaceutically acceptable salts thereof, can be used in the treatment of breast cancer, ovarian cancer, endometrial cancer, prostate cancer, uterine cancer, gastric cancer, or lung cancer.

The use of the compounds as described herein, and pharmaceutically acceptable salts thereof, for the manufacture of a medicament for treating breast cancer, ovarian cancer, endometrial cancer, prostate cancer, uterine cancer, gastric cancer, or lung cancer is further provided.

DETAILED DESCRIPTION

Novel tetracyclic compounds and pharmaceutical salts thereof that act as SERDs are disclosed herein. The newly invented SERDs that are described herein provide inhibition of ER-mediated transcription that will be useful in treating cancers such as breast cancer, ovarian cancer, endometrial cancer, prostate cancer, uterine cancer, gastric cancer, and lung cancer as well as mutations due to emerging resistance. These SERDs can be used either as single agents or in combination with other classes of drugs including selective estrogen receptor modulators (SERMs), aromatase inhibitors, CDK4 inhibitors, CDK6 inhibitors, PI3K inhibitors, and mTOR inhibitors to treat hormone receptor-positive cancers such as breast cancer, gastric cancer, and/or lung cancer.

The novel compounds described herein are represented by Formula I:

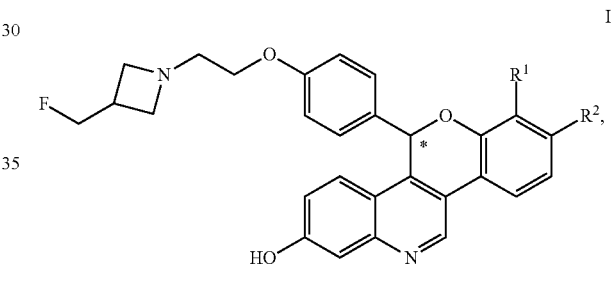

and pharmaceutically acceptable salts thereof, wherein either $R^1$ or $R^2$ is independently selected from Cl, F, —$CF_3$, or —$CH_3$, and the other is hydrogen. One of skill in the art will appreciate that compounds as described by Formula I, or pharmaceutically acceptable salts thereof, contain a chiral center, the position of which is indicated by an * above. One of skill in the art will also appreciate that the Cahn-Ingold-Prelog (R) or (S) designations for chiral centers will vary depending upon the substitution patterns around a chiral center. The chiral center in the compound of Formula I provides an R-enantiomeric form shown by Formula II:

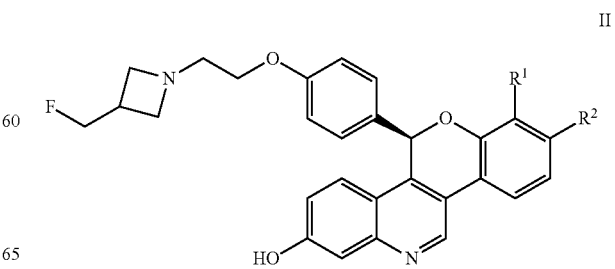

And an S-enantiomeric form shown by Formula III:

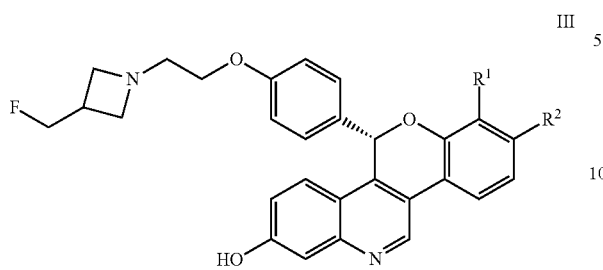

All individual stereoisomers, enantiomers, and diastereomers, as well as mixtures of the enantiomers and diastereomers of the compounds according to Formula I, Formula II, and Formula III including racemates are included within the scope of the compounds described herein. Compounds for pharmaceutical use that contain chiral centers are often isolated as single enantiomers or diastereomers and such isolated compounds of Formula I, Formula II, and Formula III are included within the scope of the compounds disclosed herein. One of skill in the art will also appreciate that the compounds of Formula I, Formula II, and Formula III described herein, and pharmaceutically acceptable salts thereof, can be deuterated (where a hydrogen can be replaced by a deuterium) and such molecules are considered to be included within the scope of the compounds disclosed herein.

Specific examples of the compounds of Formula I (including IUPAC nomenclature names) are shown here:

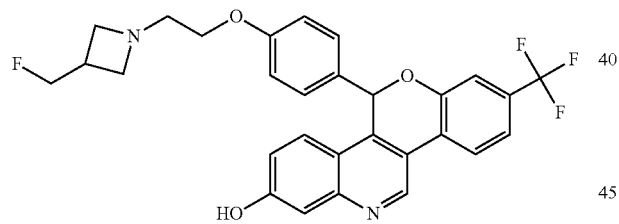

5-(4-{2-[3-(fluoromethyl)azetidin-1-yl]ethoxy}phenyl)-8-(trifluoromethyl)-5H-[1]benzopyrano[4,3-c]quinolin-2-ol;

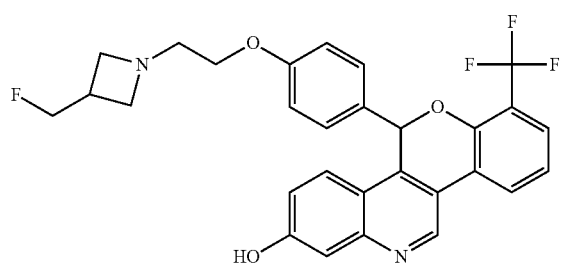 [SMILES: Oc1ccc2c3c(cnc2c1)-c1cccc(C(F)(F)F)c1OC3c1ccc(OCCN2CC(CF)C2)cc1]

5-(4-{2-[3-(fluoromethyl)azetidin-1-yl]ethoxy}phenyl)-7-(trifluoromethyl)-5H-[1]benzopyrano[4,3-c]quinolin-2-ol;

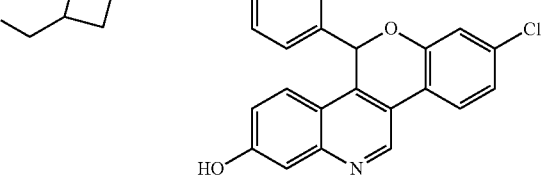

8-chloro-5-(4-{2-[3-(fluoromethyl)azetidin-1-yl]ethoxy}phenyl)-5H-[1]benzopyrano[4,3-c]quinolin-2-ol;

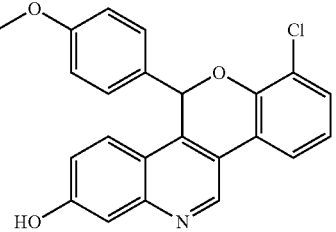

7-chloro-5-(4-{2-[3-(fluoromethyl)azetidin-1-yl]ethoxy}phenyl)-5H-[1]benzopyrano[4,3-c]quinolin-2-ol;

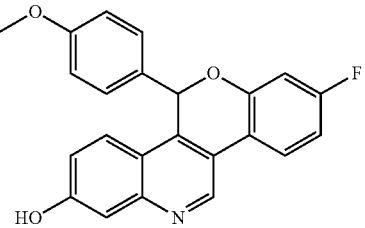

8-fluoro-5-(4-{2-[3-(fluoromethyl)azetidin-1-yl]
ethoxy}phenyl)-5H-[1]benzopyrano[4,3-c]quinolin-2-ol;

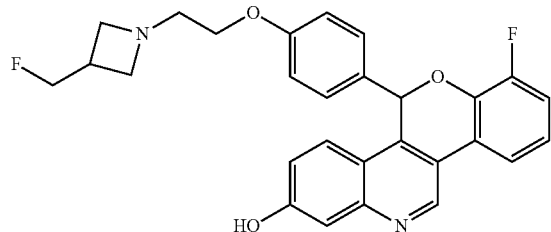 [SMILES: Oc1ccc2c3c(cnc2c1)-c1cccc(F)c1OC3c1ccc(OCCN2CC(CF)C2)cc1]

7-fluoro-5-(4-{2-[3-(fluoromethyl)azetidin-1-yl]
ethoxy}phenyl)-5H-[1]benzopyrano[4,3-c]quinolin-2-ol;

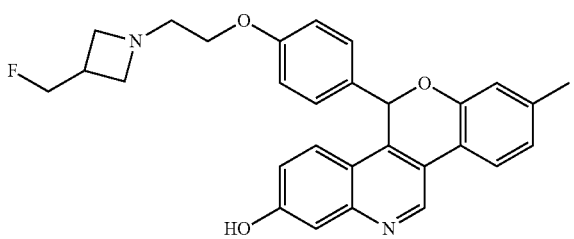 [SMILES: Cc1ccc2c(c1)OC(c1ccc(OCCN3CC(CF)C3)cc1)c1c-2cnc2cc(O)ccc12]

5-(4-{2-[3-(fluoromethyl)azetidin-1-yl]ethoxy}phenyl)-
8-methyl-5H-[1]benzopyrano[4,3-c]quinolin-2-ol; and 5-(4-{2-[3-(fluoromethyl)azetidin-1-yl]ethoxy}phenyl)-
7-methyl-5H-[1]benzopyrano[4,3-c]quinolin-2-ol.

Due to the chiral center noted above, each of these specific examples of compounds of Formula I shown above have R- and S-enantiomeric forms (i.e., R-enantiomeric compounds of Formula II and S-enantiomeric compounds of Formula III) as shown in Table 1.

TABLE 1

Enantiomeric forms of compounds of Formula I

| Chemical Name | R-enantiomer (Formula II) | S-enantiomer (Formula III) |
| --- | --- | --- |
| 5-(4-{2-[3-(fluoromethyl)azetidin-1-yl]ethoxy}phenyl)-8-(trifluoromethyl)-5H-[1]benzopyrano[4,3-c]quinolin-2-ol | | |
| 5-(4-{2-[3-(fluoromethyl)azetidin-1-yl]ethoxy}phenyl)-7-(trifluoromethyl)-5H-[1]benzopyrano[4,3-c]quinolin-2-ol | | |
| 8-chloro-5-(4-{2-[3-(fluoromethyl)azetidin-1-yl]ethoxy}phenyl)-5H-[1]benzopyrano[4,3-c]quinolin-2-ol | | |
| 7-chloro-5-(4-{2-[3-(fluoromethyl)azetidin-1-yl]ethoxy}phenyl)-5H-[1]benzopyrano[4,3-c]quinolin-2-ol | | |

TABLE 1-continued

Enantiomeric forms of compounds of Formula I

| Chemical Name | R-enantiomer (Formula II) | S-enantiomer (Formula III) |
|---|---|---|
| 8-fluoro-5-(4-{2-[3-(fluoromethyl)azetidin-1-yl]ethoxy}phenyl)-5H-[1]benzopyrano[4,3-c]quinolin-2-ol | | |
| 7-fluoro-5-(4-{2-[3-(fluoromethyl)azetidin-1-yl]ethoxy}phenyl)-5H-[1]benzopyrano[4,3-c]quinolin-2-ol | | |
| 5-(4-{2-[3-(fluoromethyl)azetidin-1-yl]ethoxy}phenyl)-8-methyl-5H-[1]benzopyrano[4,3-c]quinolin-2-ol | | |
| 5-(4-{2-[3-(fluoromethyl)azetidin-1-yl]ethoxy}phenyl)-7-methyl-5H-[1]benzopyrano[4,3-c]quinolin-2-ol | | |

Also described herein are pharmaceutical compositions including the compounds of Formula I, Formula II, and Formula III as described herein, or pharmaceutically acceptable salts thereof, in combination with a pharmaceutically acceptable excipient, carrier, or diluent. The pharmaceutical compositions described herein may be prepared using pharmaceutically acceptable additives. The term "pharmaceutically acceptable additive(s)" as used herein, refers to one or more carriers, diluents, and excipients that are compatible with the other additives of the compositions or formulations and not deleterious to the patient. The compounds of Formula I, Formula II, and Formula III, or pharmaceutically acceptable salts thereof, described herein can be formulated as pharmaceutical compositions administered by a variety of routes, such as oral or IV. Bioavailability is often a factor in cancer treatment and the ability to choose administration methods and pharmaceutical compositions to control or optimize the bioavailability of an active ingredient is useful. For example, an orally bioavailable SERD composition would be particularly useful. The compounds of Formula I, Formula II, and Formula III, or pharmaceutically acceptable salts thereof, as described herein are believed to have oral bioavailability. Examples of pharmaceutical compositions and processes for their preparation can be found in "Remington: The Science and Practice of Pharmacy", L. V. Allen Jr, Editor, 22nd Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and polyvinyl-pyrrolidone; kaolin and bentonite; and polyethyl glycols.

Further described herein are methods of treating a cancer. The methods described herein include administering to a patient in need of such treatment an effective amount of a compound of Formula I, Formula II, and Formula III as described herein, or a pharmaceutically acceptable salt thereof. For example, the method of administering the effective amount of a compound of Formula I, Formula II, and Formula III as described herein, or a pharmaceutically acceptable salt thereof, can be oral administration. The cancer can be an estrogen responsive cancer. Additionally, the cancer can be breast cancer, ovarian cancer, endometrial cancer, prostate cancer, uterine cancer, gastric cancer, or lung cancer. For example, the cancer can be ER-positive breast cancer, ER-positive gastric cancer, or ER-positive lung cancer.

Also described herein are compounds of Formula I, Formula II, and Formula III as described herein, or pharmaceutically acceptable salts thereof, for use in therapy. Also provided herein are the compounds of Formula I, Formula II, and Formula III as described herein, or pharmaceutically acceptable salts thereof, for use in the treatment of breast cancer, ovarian cancer, endometrial cancer, prostate cancer, uterine cancer, gastric cancer, or lung cancer. In particular the breast cancer can be ER-positive breast cancer, ER-positive gastric cancer, or ER-positive lung cancer. For example, the compound of Formula I, Formula II, and Formula III, or pharmaceutically acceptable salt thereof, can be orally administered.

Additionally, the compounds of Formula I, Formula II, and Formula III as described herein, or pharmaceutically acceptable salts thereof, can be used in the manufacture of a medicament for the treatment of a cancer. For example, the medicament can be orally administered. The types of cancer the medicaments as described herein can be used to treat include breast cancer, ovarian cancer, endometrial cancer, prostate cancer, uterine cancer, gastric cancer, or lung cancer. In particular the cancer can be ER-positive breast cancer, ER-positive gastric cancer, or ER-positive lung cancer.

The compounds of Formula I, Formula II, and Formula III as described herein, and pharmaceutically acceptable salts thereof, may have clinical utility as a single agent or in combination with one or more other therapeutic agents (e.g., anti-cancer agents), for the treatment of cancers such as breast cancer, ovarian cancer, endometrial cancer, prostate cancer, uterine cancer, gastric cancer, or lung cancer. When used in combination with other therapeutic agents (such as anti-cancer agents), the compounds of Formula I, Formula II, and Formula III as described herein, or pharmaceutically acceptable salts thereof, can be used simultaneously, sequentially, or separately with other therapeutic agents. Examples of classes of drugs that the compounds of Formula I, Formula II, and Formula III as described herein, or pharmaceutically acceptable salts thereof, can be combined with include SERMs, aromatase inhibitors, CDK4 inhibitors, CDK6 inhibitors, PI3K inhibitors, and mTOR inhibitors to treat hormone receptor-positive breast cancer. More specific examples of drugs with which the compounds of Formula I, Formula II, and Formula III as described herein, or pharmaceutically acceptable salts thereof, can be combined include abemaciclib (CDK4/6 inhibitor), everolimus (mTOR inhibitor), alpelisib (PIK3CA inhibitor), and 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one (PI3K/mTOR inhibitor).

As used herein, the term "effective amount" refers to the amount or dose of a compound of Formula I, Formula II, and Formula III as described herein, or a pharmaceutically acceptable salt thereof, which, upon single or multiple dose administration to the patient, provides the desired effect in the patient under diagnosis or treatment. Preferably, a desired effect is inhibition of tumor cell proliferation, tumor cell death, or both. The compounds of Formula I, Formula II, and Formula III as described herein, or pharmaceutically acceptable salts thereof, are generally effective over a wide dosage range. For example, dosages per day normally fall within the daily range of about 100 mg to about 2000 mg.

As used herein, "treat", "treating" or "treatment" refers to restraining, slowing, stopping, or reversing the progression or severity of an existing symptom or disorder.

As used herein, the term "patient" refers to a human which is afflicted with a particular disease, disorder, or condition.

The compounds of Formula I, Formula II, and Formula III as described herein, or pharmaceutically acceptable salts thereof, may be prepared by a variety of procedures known in the art, some of which are illustrated in the Preparations and Examples below. The specific synthetic steps for each of the routes described may be combined in different ways, or in conjunction with steps from different procedures, to prepare compounds of Formula I, Formula II, and Formula III as described herein, or pharmaceutically acceptable salts thereof. The products can be recovered by conventional methods well known in the art, including extraction, evaporation, precipitation, chromatography, filtration, trituration, and crystallization. The reagents and starting materials are readily available to one of ordinary skill in the art.

Intermediates and processes useful for the synthesis of the compounds of Formula I, Formula II, and Formula III as described herein are intended to be included in this description. Additionally, certain intermediates described herein may contain one or more protecting groups. The variable protecting group may be the same or different in each occurrence depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of Formula I, Formula II, and Formula III as described herein, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). While individual isomers, enantiomers, and diastereomers may be separated or resolved as noted, their Cahn-Ingold-Prelog (R) or (S) designations for chiral centers may not yet have been determined. Where Cahn-Ingold-Prelog (R) or (S) designations are not available, the identifiers "isomer 1" and "isomer 2" are used and are combined with the IUPAC name without Cahn-Ingold-Prelog stereochemistry designation. The compounds of Formula I, Formula II, and Formula III being identified as "isomer 1" or "isomer 2" herein are isolated as defined in the specific experimental descriptions below. Whether an isomer is a "1" or a "2" refers to the order in which the compounds of Formula I, Formula II, and Formula III elute from a chiral chromatography column, under the conditions listed, i.e., an "isomer 1" is the first to elute from the column under the noted conditions. If chiral chromatography is initiated early in the synthesis, the same designation is applied to subsequent intermediates and compounds of Formula I, Formula II, and Formula III.

Unless specifically noted, abbreviations used herein are defined according to *Aldrichimica Acta*, Vol. 17, No. 1, 1984. Other abbreviations are defined as follows: "ACN" refers to acetonitrile; "BSA" refers to Bovine Serum Albumin; "cataCXium® A Pd G3" refers to [(di(1-adamantyl)-butylphosphine)-2-(2'-amino-1,1'-biphenyl)]palladium(II) methanesulfonate; "DCM" refers to dichloromethane or methylene chloride; "DMA" refers to dimethylacetamide; "DMEA" refers to dimethylethylamine; "DMEM" refers to Dulbecco's Modified Eagle's Medium; "DMF" refers to N,N-dimethylformamide; "DMSO" refers to dimethyl sulfoxide; "DNA" refers to deoxyribonucleic acid; "cDNA" refers to complementary DNA; "DNase" refers to deoxyribonuclease; "DTT" refers to dithiothreitol; "$EC_{50}$" refers to the concentration of an agent which produces 50% response of the target activity compared to a predefined positive control compound (absolute $EC_{50}$); "EDTA" refers to ethylenediaminetetraacetic acid; "ee" refers to enantiomeric excess; "ERα" refers to estrogen receptor alpha; "ERβ" refers to estrogen receptor beta; "EtOAc" refers to ethyl acetate; "EtOH" refers to ethanol or ethyl alcohol; "FBS" refers to Fetal Bovine Serum; "HBSS" refers to Hank's Balanced Salt Solution; "HEC" refers to hydroxy ethyl cellulose; "HEPES" refers to 4-(2-hydroxyethyl)-1-piperazineethanesulfonic acid; "HPLC" refers to high-performance liquid chromatography; "IC$_{50}$" refers to the concentration of an agent which produces 50% of the maximal inhibitory response possible for that agent, (relative IC$_{50}$), or the concentration of an agent which produces 50% inhibition of the target enzyme activity compared to placebo control (absolute IC$_{50}$); "IPA" refers to isopropylamine; "iPrOH" refers to isopropanol or isopropyl alcohol; "IV" refers to intravenous administration; "K$_i$" refers to inhibition constant; "MEK" refers to methyl ethyl ketone; "MeOH" refers to methyl alcohol or methanol; "MTBE" refers to methyl t-butyl ether; "PBS" refers to Phosphate Buffered Saline; "PO" refers to oral administration; "PRα" refers to progesterone receptor alpha; "QD" refers to once a day dosing; "RNA" refers to ribonucleic acid; "RNase" refers to ribonuclease; "RT-PCR" refers to reverse transcription polymerase chain reaction; "RT-qPCR" refers to reverse transcription quantitative polymerase chain reaction; "SFC" refers to supercritical fluid chromatography; "TED$_{50}$" refers to the effective dose to achieve 50% inhibition of the target in the tumors; "THF" refers to tetrahydrofuran; "t$_{(R)}$" refers to retention time; "XantPhos Pd G2" refers to chloro[(4,5-bis(diphenylphosphino)-9,9-dimethylxanthene)-2-(2'-amino-1,1'-biphenyl)]palladium(II); and "XPhos Pd G2" refers to chloro(2-dicyclohexylphosphino-2',4',6'-triisopropyl-1,1'-biphenyl)[2-(2'-amino-1,1'-biphenyl)]palladium (II).

The following preparations and examples further illustrate the invention.

Preparations and Examples

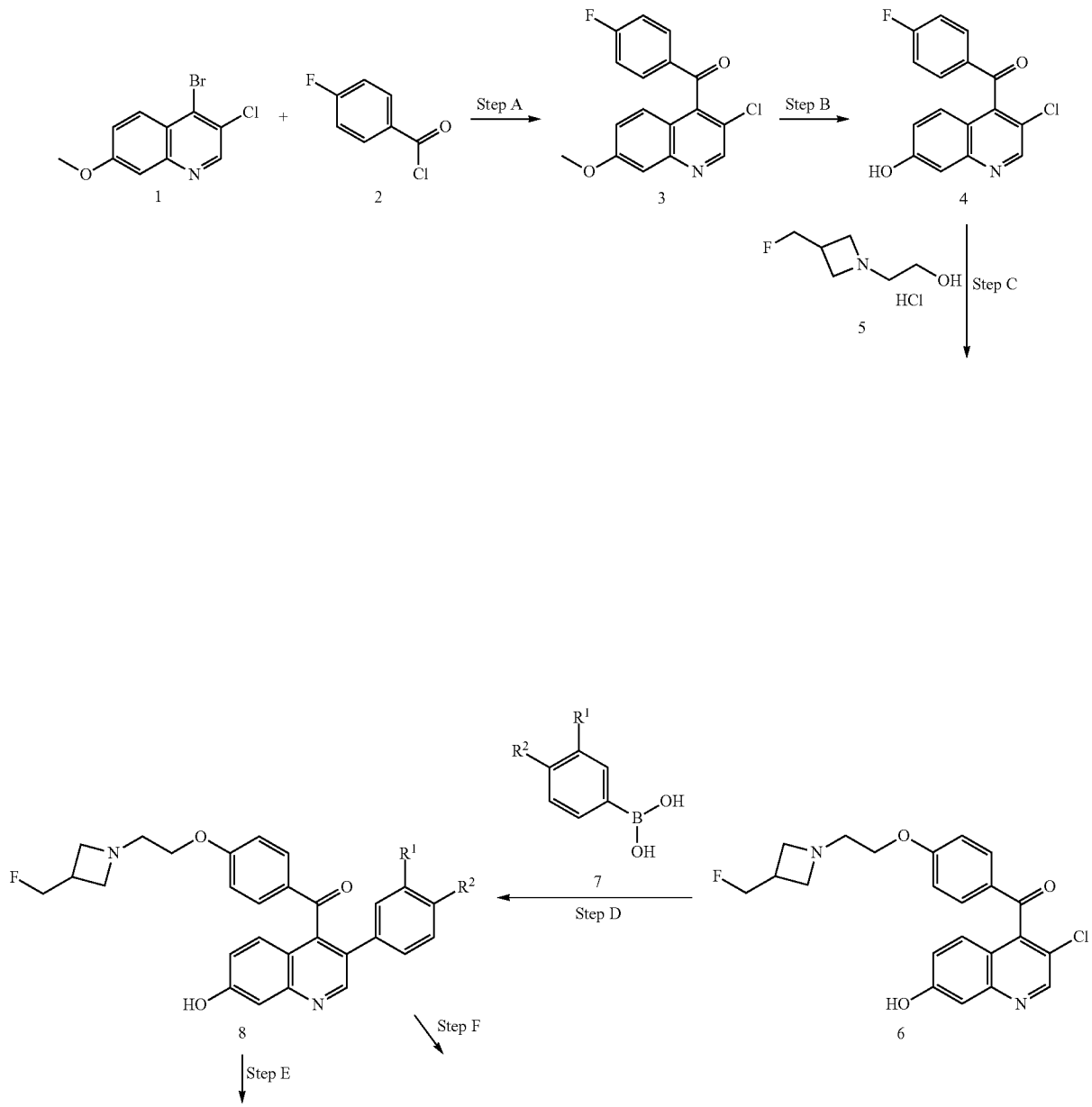

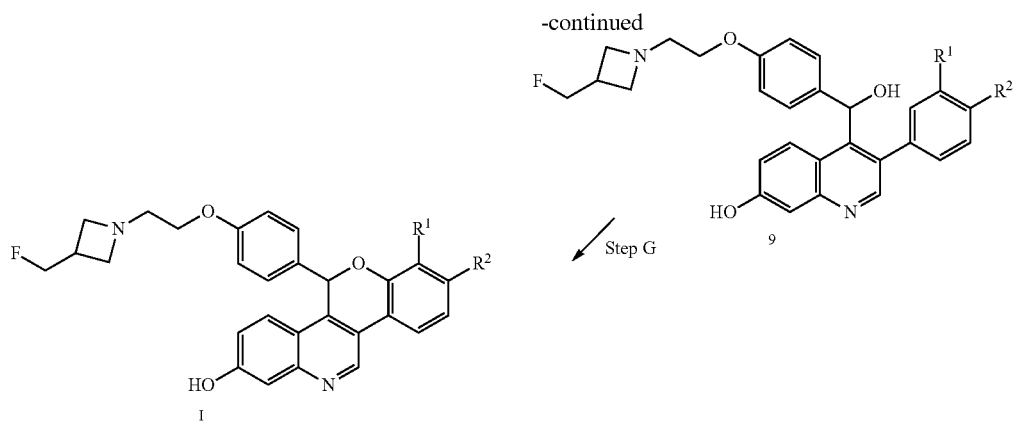

Scheme 1 depicts the synthesis of compounds of Formula I.

In Step A, a Grignard reaction is accomplished. A Grignard reaction is well known in the art as a reaction for the formation of carbon-carbon bonds. The reaction involves an organometallic reaction in which an aryl magnesium halide, the Grignard reagent adds to a carbonyl group such as the acid chloride of compound 2 to give the compound of Step A. For example, a 4-chloro-substituted quinolone, compound 1, is treated with a Grignard reagent such as isopropylmagnesium chloride to form a Grignard intermediate followed by the addition of an acid chloride, 4-fluorobenzoyl chloride, compound 2, in a solvent such as THF. At completion, the reaction can be quenched with water to give compound 3.

In Step B, the aryl methyl ether of compound 3 may be demethylated under a variety of conditions recognizable to the skilled artisan such as treatment with boron tribromide. For example, compound 3 is slowly treated with boron tribromide at a temperature of about 0° C. in a solvent such as DCM. The mixture is stirred at room temperature and quenched with dibasic potassium phosphate to give compound 4.

In Step C, the azetidine ether 6 may be formed by treatment of the corresponding p-fluorophenyl ketone 4 and the azetidine alcohol salt 5, or the corresponding free base with a suitable base, for example sodium hydride, sodium t-butoxide or potassium t-butoxide, in the appropriate polar aprotic solvent such as DMF or THF to give the ether compound 6.

Compound 6 is then alkylated with the appropriate substituted aryl boronic acid, compound 7, in a Suzuki cross coupling reaction to give compound 8 in Step D. The skilled artisan will recognize that there are a variety of conditions that may be useful for facilitating such cross-coupling reactions. Suitable palladium reagents may include Xant-Phos Pd G2, cataCXium® A Pd G3, bis(triphenylphosphine)palladium(II) chloride, tris(dibenzylideneacetone)dipalladium (0) with tricyclohexylphosphine, (1,1'-bis(diphenylphosphino)ferrocene)palladium(II) chloride, palladium tetrakistriphenylphosphine, or palladium(II) acetate. Suitable bases may include potassium fluoride, cesium carbonate, sodium carbonate, potassium carbonate, lithium t-butoxide, or potassium phosphate tribasic monohydrate. Compound 6, for example, can be reacted with the appropriate boronic acid, compound 7, such as 2-fluoro-4-(trifluoromethyl)phenylboronic acid in a solvent such as 2-methyl-2-butanol with a base such as potassium carbonate and a catalyst such as XPhos Pd G2 and heated to about 80° C. under microwave conditions to give compound 8.

One skilled in the art will recognize that Step D, the Suzuki cross coupling reaction, could be completed before the azetidine ether formation of Step C.

In Step E, one skilled in the art will recognize that compound 8 may be cyclized by the initial reduction of the ketone. This can be accomplished using a reducing agent, such as lithium triethyl borohydride in solvents such as 1,4-dioxane and THF and at a temperature of about 0° C. to room temperature to give the corresponding secondary alcohol. This intermediate alcohol can be carried on crude and be deprotonated with a suitable base such as cesium carbonate, sodium hydride, sodium t-butoxide or potassium t-butoxide in a solvent such as THF, DMSO, or DMF. The resulting alkoxide can cyclize into the aryl fluoride at room temperature, with heating to reflux, or at a temperature of about 60° C. The substituted cyclic ether formed upon displacement of the fluoride can then be obtained to give compounds of Formula I.

Alternatively, the ketone, 8, can be reduced to the alcohol and chirally purified at Step F to give the chiral alcohol 9, and then cyclized in Step G as described above for Step E to give compounds of Formula I.

In another alternative reaction, the ketone can be reduced using a chiral reagent such as (R)-(+)-α.α-diphenyl-2-pyrrolidinemethanol along with trimethyl borate and borane-dimethylsulfide to directly give the desired chiral alcohol, compound 9 which can then be cyclized in Step G as described above for Step E to give compounds of Formula I.

In an optional step, a pharmaceutically acceptable salt of a compound of Formula I, Formula II, and Formula III as described herein can be formed by reaction of an appropriate free base of a compound of Formula I, Formula II, and Formula III as described herein with an appropriate pharmaceutically acceptable acid in a suitable solvent under standard conditions. Additionally, the formation of such salts can occur simultaneously upon deprotection of a nitrogen-protecting group. The possible formation of pharmaceutically acceptable salts is well known. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that a compound of Formula I, Formula II, and Formula III as described herein is readily converted to and may be isolated as a pharmaceutically acceptable salt. Examples of useful salts include, but are not limited to, benzenesulfonic acid salts and 4-methybenzenesulfonic acid salts. 4-methylbenzenesulfonic acid salts are also known as tosylate salts.

Preparation 1

2-[3-(Fluoromethyl)azetidin-1-yl]ethan-1-ol

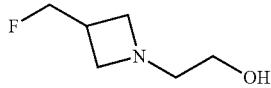

Add sodium triacetoxyborohydride (405 g, 1.91 mol) portion-wise over a period of 15 minutes to a stirred 0° C. solution of 3-(fluoromethyl)azetidine hydrochloride (160 g, 1.28 mol) in DCM (2.4 L) under $N_2$ and stir at 0° C. for 10 minutes. Add 1,4-dioxane-2,5-diol (99 g, 0.83 mol) at 0° C. in 6 portions over a period of 1 hour then stir at 0-5° C. for 15 minutes. Allow the reaction to warm to room temperature and stir for 2 hours under $N_2$. Cool the reaction to 10-15° C. over a period of 20 minutes, then warm to 25-30° C. and maintain at this temperature for 2 hours. Add water (800 mL) over a period of 25-30 minutes at 10-15° C., allow to warm to room temperature for 5-10 minutes and then separate the layers. Wash the aqueous layer with DCM (800 mL), separate the layers then cool the combined aqueous layers to 10-15° C. and adjust the pH to 13-14 using 50% sodium hydroxide solution (~540 mL). Allow the aqueous layer to warm to room temperature, extract with DCM (4×800 mL), dry with sodium sulfate (80 g), filter, and concentrate to dryness to obtain the title compound (139 g, 82%) as a thick yellow oil. ES/MS (m/z): 134.1 (M+H).

Preparation 2

2-[3-(Fluoromethyl)azetidin-1-yl]ethan-1-ol hydrochloride

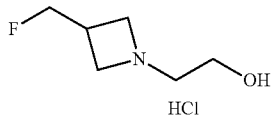

Dissolve 2-[3-(fluoromethyl)azetidin-1-yl]ethan-1-ol (529 g, 4 mol) in MTBE (2.6 L) and cool to 0° C. Add HCl/EtOH solution (492 mL, 30 wt %) drop-wise over 30 minutes then stir at 0° C. for 30 minutes. Filter the solids and wash the filter cake with MTBE (2×200 mL). Dry under $N_2$ for 8 hours to obtain the title compound (580 g, 86%) as a white solid. ES/MS (m/z): 134.0 (M+H).

Preparation 3

(3-Chloro-7-methoxyquinolin-4-yl)-(4-fluorophenyl)methanone

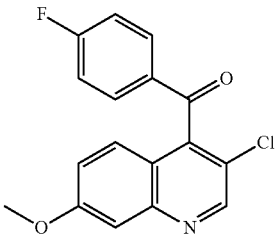 [SMILES: COc1ccc2c(C(=O)c3ccc(F)cc3)c(Cl)cnc2c1]

Cool a mixture of 4-bromo-3-chloro-7-methoxyquinoline (70 g, 254 mmol) and THF (1 L) to −40° C. under $N_2$ resulting in precipitation of the material. Add isopropylmagnesium chloride (2 M in THF, 254 mL, 509 mmol) over 20 minutes and stir the mixture for 1 hour. Add a solution of 4-fluorobenzoyl chloride (66 mL, 559 mmol) in THF (140 mL) drop-wise then allow to warm to room temperature. Quench the reaction with saturated $NH_4Cl$ solution (300 mL) and water (200 mL) and separate the layers. Wash the organic layer with saturated $NH_4Cl$ solution (300 mL), dry over $MgSO_4$, filter, and concentrate to provide an oily residue. Filter the crude brown oil through silica gel eluting with a mixture of MTBE/hexanes (1:1) to obtain the crude product as a yellow solid (84 g). Treat the solid with 10% methylacetate/heptane (800 mL) and stir at room temperature overnight. Filter to collect the solids and reserve. Concentrate the filtrate and purify on silica gel eluting with 10-40% EtOAc/hexanes then treat the product with 10% methylacetate/heptane (200 mL) and stir at room temperature for 3 hours. Filter the resulting solids, combine with solids from the previous filtration and dry under vacuum overnight to obtain the title compound (31 g, 38%) as a yellow solid. ES/MS (m/z): 316.0 (M+H).

Preparation 4

(3-Chloro-7-hydroxyquinolin-4-yl)-(4-fluorophenyl)methanone

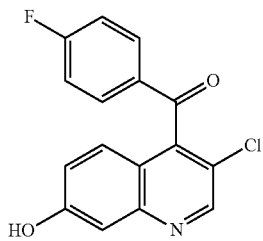 [SMILES: O=C(c1ccc(F)cc1)c1c(Cl)cnc2cc(O)ccc12]

Add boron tribromide (1 M in DCM, 295 mL, 295 mmol) to a mixture of (3-chloro-7-methoxyquinolin-4-yl)-(4-fluorophenyl)methanone (31 g, 98 mmol) in DCM (217 ml) and stir the mixture at room temperature for 3 days. Pour the mixture slowly into a 0° C. solution of dibasic potassium phosphate (2 M in water, 700 mL) and water (200 mL). Allow the mixture to warm to room temperature and stir for 1 hour. Concentrate the solution in vacuo to remove organic solvents, filter, collect the filtrate and dry the filtrate under vacuum at 45° C. overnight. Treat the solids with DCM/heptane (1:1, 450 mL) and stir overnight. Collect the solids and dry under vacuum overnight to obtain the title compound (32 g, quantitative yield) as a light brown solid. ES/MS (m/z): 302.0 (M+H).

Preparation 5

(3-Chloro-7-hydroxyquinolin-4-yl)-(4-{2-[3-(fluoromethyl)azetidin-1-yl]ethoxy}phenyl)methanone

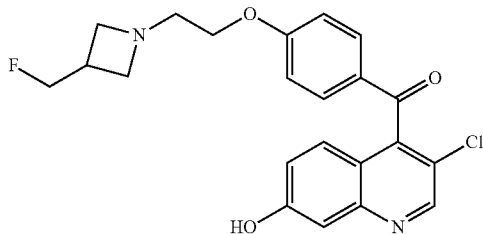 [SMILES: O=C(c1ccc(OCCN2CC(CF)C2)cc1)c1c(Cl)cnc2cc(O)ccc12]

Add 2-[3-(fluoromethyl)azetidin-1-yl]ethan-1-ol hydrochloride (3.90 g, 23.0 mmol) to a stirred solution of (3-chloro-7-hydroxyquinolin-4-yl)-(4-fluorophenyl)methanone (5.00 g, 15.3 mmol) in DMF (75 ml) followed by sodium hydride (60% in mineral oil, 3.02 g, 76.8 mmol). Stir under $N_2$ and warm to 40° C. for 45 minutes. Quench the solution with water and concentrate. Partition the residue between 20% iPrOH/CHCl$_3$ and saturated aqueous sodium bicarbonate solution and separate, extract the aqueous with 2×20% iPrOH/CHCl$_3$, combine the organic extracts, dry the combined organic layers over magnesium sulfate, filter and concentrate the filtrate to obtain the crude product as a dark red oil. Purify the crude material by silica gel column chromatography eluting with a gradient of 5-10% 7 N NH$_3$ in MeOH/DCM to give the title compound (5.31 g, 84%) as a yellow solid. ES/MS (m/z): 415.0 (M+H).

Preparation 6

(4-{2-[3-(Fluoromethyl)azetidin-1-yl]ethoxy}phenyl){3-[2-fluoro-4-(trifluoromethyl)phenyl]-7-hydroxyquinolin-4-yl}methanone

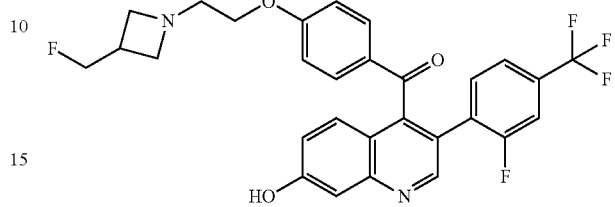

Degas with $N_2$ (5×) a mixture (3-chloro-7-hydroxyquinolin-4-yl)-(4-{2-[3-(fluoromethyl)azetidin-1-yl]ethoxy}phenyl)methanone (200 mg, 0.48 mmol), 2-fluoro-4-(trifluoromethyl)phenylboronic acid (158 mg, 0.72 mmol), potassium carbonate (202 mg, 1.45 mmol), 2-methyl-2-butanol (3 ml), and water (1 ml) in a microwave vial. Add XPhos Pd G2 (12 mg, 0.015 mmol), seal and microwave at 80° C. for 2 hours. Partition the residue between MTBE and saturated NH$_4$Cl solution. Separate the layers and extract the aqueous with MTBE. Combine the organic extracts, dry over magnesium sulfate, filter, and concentrate the filtrate to obtain an orange residue. Purify the crude material by silica gel column chromatography eluting with 5% MeOH/DCM to give the title compound (205 mg, 78%) as a yellow solid. ES/MS (m/z): 543.2 (M+H).

Prepare the following compounds in a manner essentially analogous to the method of Preparation 6, with the following variations in procedure, heating times between 1-2 hours, extraction with MTBE or EtOAc, and drying of organic layers over magnesium sulfate or sodium sulfate. Purify by silica gel column chromatography using up to 10% (MeOH or 7 M ammoniated MeOH) in DCM (Prep 10: gradient 3-8% 7 M ammoniated MeOH in DCM; Preps 9 and 11: gradient 4 to 10% 7 M ammoniated MeOH in DCM) and/or by high pH reversed phase chromatography as noted.

TABLE 2

Compounds prepared according to Preparation 6

| Prep No. | Chemical Name | Structure | ES/MS (m/z) (M + H) |
|---|---|---|---|
| 7 | (4-{2-[3-(Fluoromethyl)azetidin-1-yl]ethoxy}phenyl){3-[2-fluoro-3-(trifluoromethyl)phenyl]-7-hydroxyquinolin-4-yl}methanone | 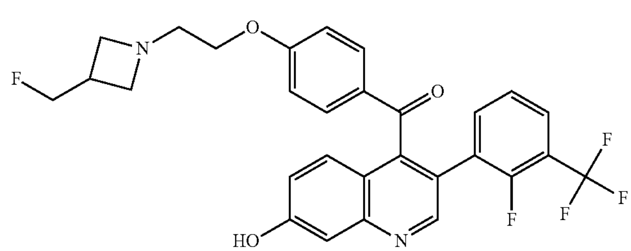 [SMILES: O=C(c1ccc(OCCN2CC(CF)C2)cc1)c1c(-c2cccc(C(F)(F)F)c2F)cnc2cc(O)ccc12] | 543.0 |

TABLE 2-continued

Compounds prepared according to Preparation 6

| Prep No. | Chemical Name | Structure | ES/MS (m/z) (M + H) |
|---|---|---|---|
| 8[a] | [3-(4-Chloro-2-fluorophenyl)-7-hydroxyquinolin-4-yl](4-{2-[3-(fluoromethyl)azetidin-1-yl]ethoxy}phenyl)methanone | 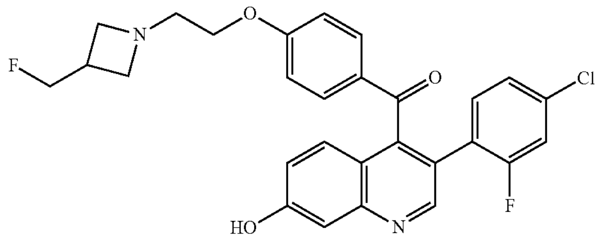 [SMILES: O=C(c1ccc(OCCN2CC(CF)C2)cc1)c1c(-c2ccc(Cl)cc2F)cnc2cc(O)ccc12] | 509.0 |
| 9[b] | [3-(3-Chloro-2-fluorophenyl)-7-hydroxyquinolin-4-yl](4-{2-[3-(fluoromethyl)azetidin-1-yl]ethoxy}phenyl)methanone | 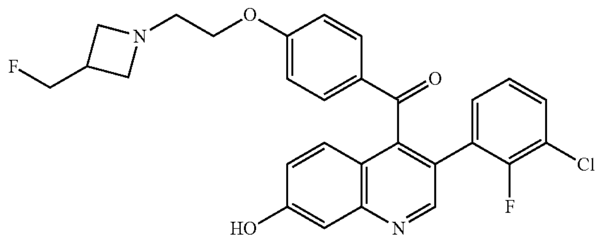 [SMILES: O=C(c1ccc(OCCN2CC(CF)C2)cc1)c1c(-c2cccc(Cl)c2F)cnc2cc(O)ccc12] | 509.0 |
| 10 | [3-(2,4-Difluorophenyl)-7-hydroxyquinolin-4-yl](4-{2-[3-(fluoromethyl)azetidin-1-yl]ethoxy}phenyl)methanone | 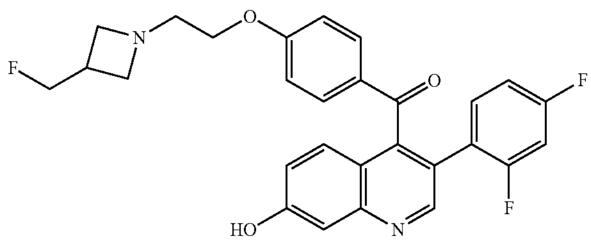 [SMILES: O=C(c1ccc(OCCN2CC(CF)C2)cc1)c1c(-c2ccc(F)cc2F)cnc2cc(O)ccc12] | 493.0 |
| 11 | [3-(2,3-Difluorophenyl)-7-hydroxyquinolin-4-yl](4-{2-[3-(fluoromethyl)azetidin-1-yl]ethoxy}phenyl)methanone | 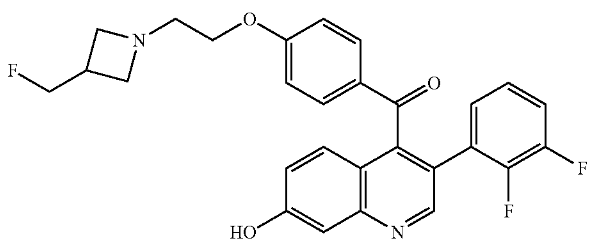 [SMILES: O=C(c1ccc(OCCN2CC(CF)C2)cc1)c1c(-c2cccc(F)c2F)cnc2cc(O)ccc12] | 493.0 |
| 12 | (4-{2-[3-(Fluoromethyl)azetidin-1-yl]ethoxy}phenyl)[3-(2-fluoro-4-methylphenyl)-7-hydroxyquinolin-4-yl]methanone | 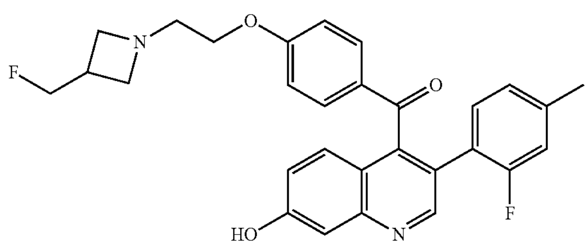 [SMILES: Cc1ccc(-c2cnc3cc(O)ccc3c2C(=O)c2ccc(OCCN3CC(CF)C3)cc2)c(F)c1] | 489.2 |
| 13 | (4-{2-[3-(Fluoromethyl)azetidin-1-yl]ethoxy}phenyl)[3-(2-fluoro-3-methylphenyl)-7-hydroxyquinolin-4-yl]methanone | 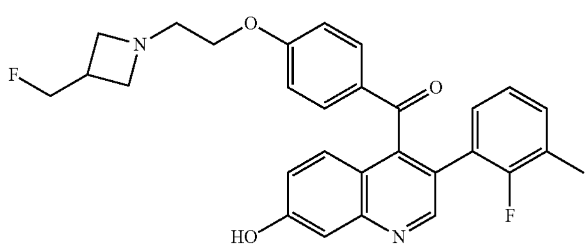 [SMILES: Cc1cccc(-c2cnc3cc(O)ccc3c2C(=O)c2ccc(OCCN3CC(CF)C3)cc2)c1F] | 489.2 |

[a]Purify by high pH reversed phase flash chromatography (RediSep Rf GOLD ® High Performance C18 column, eluting with 35-45% ACN in 10 mM aqueous ammonium bicarbonate with 5% MeOH).
[b]After purification on silica elute with 4-10% 7 M ammoniated MeOH in DCM, further purify by high pH reversed phase flash chromatography (RediSep Rf GOLD ® High Performance C18 column, eluting with 30-44% ACN in 10 mM aqueous ammonium bicarbonate with 5% MeOH).

Preparation 14

Racemic 4-{2-[3-(Fluoromethyl)azetidin-1-yl]
ethoxy}phenyl)(hydroxy)methyl]-3-[2-fluoro-4-(trifluoromethyl)phenyl]quinolin-7-ol

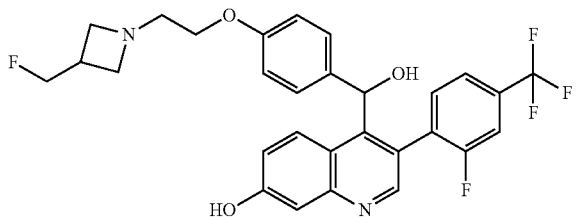 [SMILES: Oc1ccc2c(C(O)c3ccc(OCCN4CC(CF)C4)cc3)c(-c3ccc(C(F)(F)F)cc3F)cnc2c1]

Add (4-{2-[3-(fluoromethyl)azetidin-1-yl] ethoxy}phenyl){3-[2-fluoro-4-(trifluoromethyl)phenyl]-7-hydroxyquinolin-4-yl}methanone (305 g, 562.2 mmol) and THF (1.5 L) together under N₂ and cool the solution to 0-5° C. Add lithium triethylborohydride (1 M in THF, 1.5 L, 1.5 mol) dropwise. Stir the mixture at 0-5° C. for 1 hour. Add water (300 mL) dropwise and saturated NH₄Cl (1 L). Warm the mixture to room temperature. Add EtOAc (2 L) and collect the organic layer. Wash the organic layer with brine (500 mL), dry over MgSO₄, filter, and concentrate to dryness. Dissolve the residue in 95:5 mixture of acetone and 2 M ammonia in MeOH and filter through silica gel to give the title compound (264 g, 86.2%) as an orange solid. ES/MS (m/z): 545.2 (M+H).

Preparation 15

4-{2-[3-(Fluoromethyl)azetidin-1-yl]ethoxy}phenyl)(hydroxy)methyl]-3-[2-fluoro-4-(trifluoromethyl)phenyl]quinolin-7-ol, Isomer 1

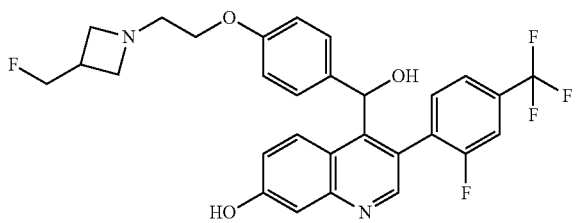 [SMILES: Oc1ccc2c(C(O)c3ccc(OCCN4CC(CF)C4)cc3)c(-c3ccc(C(F)(F)F)cc3F)cnc2c1]

Purify Racemic 4-{2-[3-(fluoromethyl)azetidin-1-yl]ethoxy}phenyl)(hydroxy)methyl]-3-[2-fluoro-4-(trifluoromethyl)phenyl]quinolin-7-ol (354 g, 0.62 mol) using chiral chromatography under the following conditions: Column Chiralpak AD-H, 150×50 mm, flow rate 300 g/minute, UV 350 nm, mobile phase 35% iPrOH with 0.5% DMEA/CO₂, column temperature 40° C. to give the title compound (171.4 g, 48%) of the first eluting isomer. Confirm enantiomeric enrichment of Isomer 1 by chiral analytical SFC, >98% ee, $t_{(R)}$=0.79 minutes, column: 4.6×150 mm Chiralpak AD-H, eluting with a mobile phase of 35% iPrOH with 0.5% DMEA in CO₂, flow rate of 0.6 mL/minute, UV detection of 350 nm.

Alternate Preparation 15

Add trimethyl borate (65 mg, 0.62 mmol) to a solution of (R)-(+)-α,α-diphenyl-2-pyrrolidinemethanol (132 mg, 0.52 mmol) in THF (20 mL). Stir the mixture under N₂ at room temperature for 1 hour. Add borane-dimethylsulfide (2.0 M in THF, 2.6 mL, 5.2 mmol) followed by (4-{2-[3-(fluoromethyl)azetidin-1-yl]ethoxy}phenyl){3-[2-fluoro-4-(trifluoromethyl)phenyl]-7-hydroxyquinolin-4-yl}methanone (1.0 g, 1.73 mmol). Heat the reaction overnight at 45° C. Add additional borane-dimethylsulfide (2.0 M in THF, 2.6 mL, 5.2 mmol) and stir for 5 hours at 45° C. Slowly add saturated NH₄Cl solution (25 mL) and isolate the organic phase. Re-extract the aqueous extract with 20% iPrOH/CHCl₃. Combine the organic extracts, dry over Na₂SO₄, filter, and evaporate to give a borane complex intermediate (1.2 g). Dissolve one third of the borane complex intermediate (0.4 g, 0.6 mmol) in 1,4-dioxane (4 mL) and ethanolamine (0.3 mL, 5 mmol) and heat the reaction to 70° C. for 3 hours. Quench the reaction with saturated NH₄Cl solution (25 mL) and isolate the organic phase. Re-extract the aqueous extract with 20% iPrOH/CHCl₃ (4×25 mL). Combine the organic extracts, dry over Na₂SO₄, filter, and concentrate to dryness to give the title compound as an orange solid (0.33 g, 0.57 mmol, 100% yield). LC/MS (m/z): [M+H]⁺ 545. Confirm enantiomeric enrichment of Isomer 1 by chiral analytical SFC, 96% ee, $t_{(R)}$=0.79 minutes, column: 4.6×150 mm Chiralpak AD-H, eluting with a mobile phase of 35% iPrOH with 0.5% DMEA in CO₂, flow rate of 0.6 mL/minute, UV detection of 350 nm.

Example 1

Racemic 5-(4-{2-[3-(Fluoromethyl)azetidin-1-yl]ethoxy}phenyl)-8-(trifluoromethyl)-5H-[1]benzopyrano[4,3-c]quinolin-2-ol

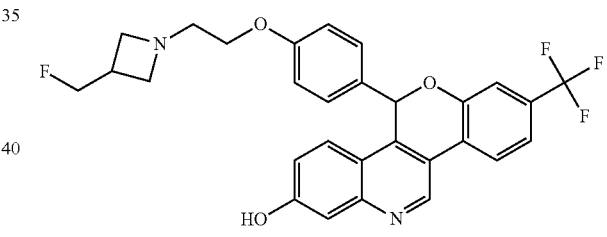

Cool a solution of (4-{2-[3-(fluoromethyl)azetidin-1-yl]ethoxy}phenyl){3-[2-fluoro-4-(trifluoromethyl)phenyl]-7-hydroxyquinolin-4-yl}methanone (5.27 g, 9.71 mmol) in 1,4-dioxane (100 mL) to 5° C. Add lithium triethylborohydride (1 M in THF, 30.0 mL, 30.0 mmol). Remove the cooling bath and stir for 1.5 hours at room temperature. Quench the mixture with water. Add saturated NH₄Cl solution and EtOAc. Separate the layers and extract the aqueous layer with EtOAc. Combine the organic extracts, dry over anhydrous MgSO₄, filter, and concentrate the filtrate. Dissolve the crude residue in THF (100 mL). Add sodium hydride (60% in mineral oil, 1.94 g, 48.5 mmol). Reflux the solution for 1.5 hours. Add additional sodium hydride (60% in mineral oil, 1.94 g, 48.5 mmol), then reflux for an additional 30 minutes. Cool the solution to room temperature and quench with water. Add EtOAc and saturated NH₄Cl solution. Separate the layers and extract the aqueous layer with EtOAc. Combine the organic extract, dry over anhydrous MgSO₄, filter, and concentrate the filtrate. Purify the residue by silica gel column chromatography eluting with a gradient of 5-7% MeOH in DCM to give the title compound (3.70 g, 72%) as a light yellow foam. ES/MS (m/z): 525.2 (M+H).

Prepare the following compounds in a manner essentially analogous to the method of Example 1, with the following variations in procedure. For the reduction, use 3 to 5 equivalents of lithium triethylborohydride with reaction times from 30 minutes to one hour and drying of the organic layers over magnesium sulfate or sodium sulfate. Use the crude residue directly or purify by silica gel column chromatography eluting with a gradient of 0-5-7.5-10% MeOH in DCM before cyclization. Complete the cyclization by refluxing in THF for up to 16 hours, or in DMF, from 2 hours at room temperature for Ex 2, to 2 hours at 85° C. for Ex 8. Extract with DCM or EtOAc and dry organic layers over magnesium sulfate or sodium sulfate. Purify by silica gel column chromatography using up to 10% (MeOH or 7 M ammoniated MeOH) in DCM (Ex 2: gradient 0-10% MeOH in DCM; Ex 5: gradient 4-10% 7 M ammoniated MeOH in DCM; Ex 8: gradient 5-7.5% 7 M ammoniated MeOH in DCM) or by high pH reversed phase HPLC as noted.

TABLE 3

Example Compounds prepared according to Example 1

| Ex No. | Chemical Name | Structure | ES/MS (m/z) (M + H) |
|---|---|---|---|
| 2 | Racemic 5-(4-{2-[3-(fluoromethyl)azetidin-1-yl]ethoxy}phenyl)-7-(trifluoromethyl)-5H-[1]benzopyrano[4,3-c]quinolin-2-ol | 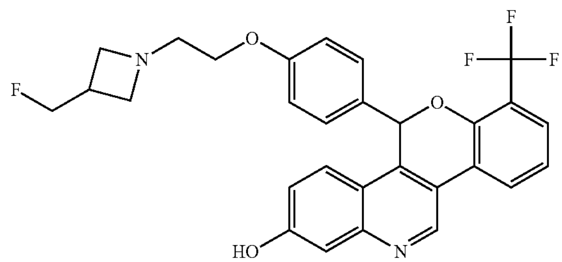 [SMILES: Oc1ccc2c3c(cnc2c1)-c1cccc(C(F)(F)F)c1OC3c1ccc(OCCN2CC(CF)C2)cc1] | 525.2 |
| 3[a] | Racemic 8-chloro-5-(4-{2-[3-(fluoromethyl)azetidin-1-yl]ethoxy}phenyl)-5H-[1]benzopyrano[4,3-c]quinolin-2-ol | 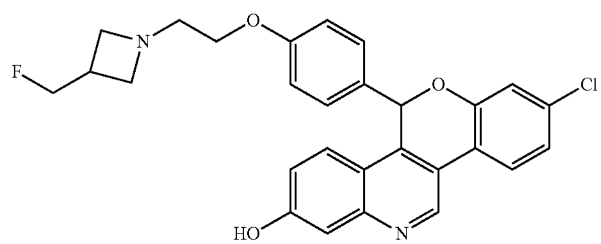 [SMILES: Oc1ccc2c3c(cnc2c1)-c1ccc(Cl)cc1OC3c1ccc(OCCN2CC(CF)C2)cc1] | 491.0 |
| 4[b] | Racemic 7-chloro-5-(4-{2-[3-(fluoromethyl)azetidin-1-yl]ethoxy}phenyl)-5H-[1]benzopyrano[4,3-c]quinolin-2-ol | 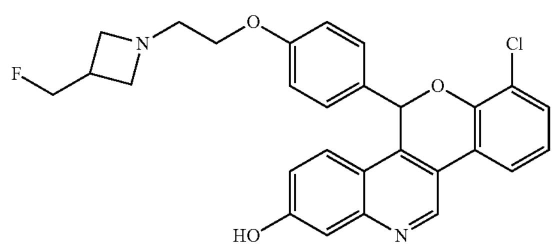 | 491.0 |
| 5[c] | Racemic 8-fluoro-5-(4-{2-[3-(fluoromethyl)azetidin-1-yl]ethoxy}phenyl)-5H-[1]benzopyrano[4,3-c]quinolin-2-ol | 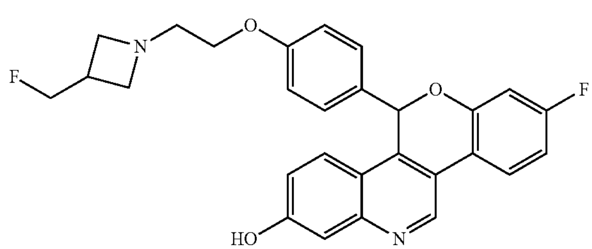 [SMILES: Oc1ccc2c3c(cnc2c1)-c1ccc(F)cc1OC3c1ccc(OCCN2CC(CF)C2)cc1] | 475.0 |
| 6[d] | Racemic 7-fluoro-5-(4-{2-[3-(fluoromethyl)azetidin-1-yl]ethoxy}phenyl)-5H-[1]benzopyrano[4,3-c]quinolin-2-ol | 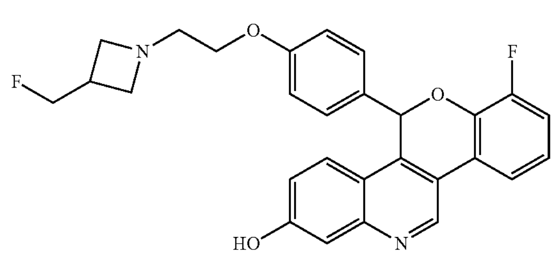 | 475.0 |

TABLE 3-continued

Example Compounds prepared according to Example 1

| Ex No. | Chemical Name | Structure | ES/MS (m/z) (M + H) |
|---|---|---|---|
| 7[e] | Racemic 5-(4-{2-[3-(fluoromethyl)azetidin-1-yl]ethoxy}phenyl)-8-methyl-5H-[1]benzopyrano[4,3-c]quinolin-2-ol | 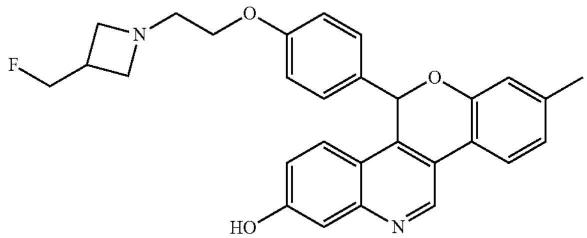 [SMILES: Cc1ccc2c(c1)OC(c1ccc(OCCN3CC(CF)C3)cc1)c1c-2cnc2cc(O)ccc12] | 471.2 |
| 8 | Racemic 5-(4-{2-[3-(fluoromethyl)azetidin-1-yl]ethoxy}phenyl)-7-methyl-5H-[1]benzopyrano[4,3-c]quinolin-2-ol | 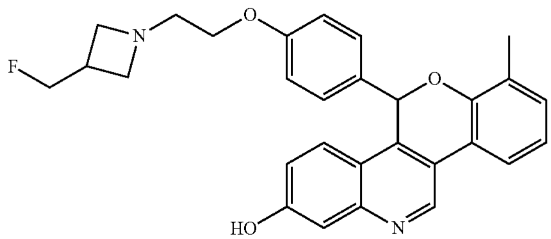 | 471.2 |

[a] Purify by high pH reversed phase HPLC (KINETEX ® C18, 5 μm, 30 × 250 mm column, eluting with 35-50% ACN in 10 mM aqueous ammonium bicarbonate with 5% MeOH).
[b] Purify by high pH reversed phase HPLC (KINETEX ® C18, 5 μm, 30 × 250 mm column, eluting with 35-43% ACN in 10 mM aqueous ammonium bicarbonate with 5% MeOH)
[c] After purification on silica eluting with 4-10% 7M ammoniated MeOH in DCM, further purify by high pH reversed phase HPLC (KINETEX ® C18, 5 μm, 30 × 250 mm column, eluting with 30-44% ACN in 10 mM aqueous ammonium bicarbonate with 5% MeOH).
[d] Purify by high pH reversed phase HPLC (XBRIDGE ® C18 5 μm OBD, 30 × 75 mm column, eluting with 10-75% ACN in 10 mM aqueous ammonium bicarbonate with 5% MeOH).
[e] Purify by high pH reversed phase HPLC (XBRIDGE ® C18 5 μm OBD, 30 × 75 mm column, eluting with 10-60% ACN in 10 mM aqueous ammonium bicarbonate with 5% MeOH).

Example 1A 5-(4-{2-[3-(Fluoromethyl)azetidin-1-yl]ethoxy}phenyl)-8-(trifluoromethyl)-5H-[1]benzopyrano[4,3-c]quinolin-2-ol, Isomer 1 and

Example 1B 5-(4-{2-[3-(Fluoromethyl)azetidin-1-yl]ethoxy}phenyl)-8-(trifluoromethyl)-5H-[1]benzopyrano[4,3-c]quinolin-2-ol, Isomer 2

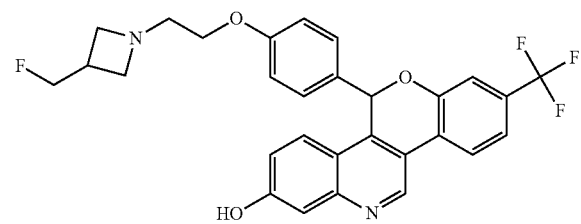 [SMILES: Oc1ccc2c3c(cnc2c1)-c1ccc(C(F)(F)F)cc1OC3c1ccc(OCCN2CC(CF)C2)cc1]

Separate the two enantiomers of 5-(4-{2-[3-(fluoromethyl)azetidin-1-yl]ethoxy}phenyl)-8-(trifluoromethyl)-5H-[1]benzopyrano[4,3-c]quinolin-2-ol by chiral SFC with the following conditions: Column: LUX® Cellulose-1, 5×25 cm; eluting with a mobile phase of 30% iPrOH (with 0.5% DMEA) in $CO_2$; column temperature: 40° C.; flow rate: 300 g/minute; UV detection wavelength: 270 nm to give Example 1A as the first eluting enantiomer (Isomer 1). ES/MS (m/z): 525.2 (M+H). Confirm enantiomeric enrichment of Isomer 1 by chiral analytical SFC, >99% ee, $t_{(R)}$: 1.30 minutes; column: CHIRALCEL® OD-H, 4.6×150 mm; eluting with a mobile phase of 30% MeOH (0.2% IPA) in $CO_2$; column temperature: 40° C.; flow rate: 5 mL/minute; UV detection wavelength: 225 nm. Isolate the title compound of Example 1B to give the second eluting enantiomer (Isomer 2). ES/MS (m/z): 525.2 (M+H). Confirm enantiomeric enrichment of Isomer 2 by chiral analytical SFC, 98% ee, $t_{(R)}$: 2.03 minutes; column: CHIRALCEL® OD-H, 4.6× 150 mm; eluting with a mobile phase of 30% MeOH (0.2% IPA) in $CO_2$; column temperature: 40° C.; flow rate: 5 mL/minute; UV detection wavelength: 225 nm.

Alternate Preparation Example 1B

Crystalline 5-(4-{2-[3-(Fluoromethyl)azetidin-1-yl]ethoxy}phenyl)-8-(trifluoromethyl)-5H-[1]benzopyrano[4,3-c]quinolin-2-ol, Isomer 2

Stir 5-(4-{2-[3-(fluoromethyl)azetidin-1-yl]ethoxy}phenyl)-8-(trifluoromethyl)-5H-[1]benzopyrano[4,3-c]quinolin-2-ol, 4-methylbenzenesulfonic acid, Isomer 2 (23.8 g, 0.034 mol) in water (250 mL) at 1000 rpm. Add NaOH (76 μL) and stir the solution for 2 hours. Add DCM (600 mL). Separate the mixture, dry the DCM extract with magnesium sulfate, filter the material through a syringe filter (0.45 μm), and concentrate to dryness. Allow the material to sit under a $N_2$ stream over a weekend. Add 1:1 EtOH/water (80 mL) and stir the mixture with sonication. Collect a tan solid by filtration on a nylon membrane to give the title compound (10.47 g, 0.02 mol, 59%).

X-Ray Powder Diffraction (XRD)

The XRPD patterns of crystalline solids are obtained on a Bruker D4 Endeavor X-ray powder diffractometer, equipped with a CuKα source and a Vantec detector, operating at 35 kV and 50 mA. The sample is scanned between 4 and 40 2θ°, with a step size of 0.008 2θ° and a scan rate of 0.5 seconds/step, and using 1.0 mm divergence, 6.6 mm fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

Characterize a prepared sample of crystalline 5-(4-{2-[3-(fluoromethyl)azetidin-1-yl]ethoxy}phenyl)-8-(trifluoromethyl)-5H-[1]benzopyrano[4,3-c]quinolin-2-ol, Isomer 2 by an XRD pattern using CuKα radiation as having diffraction peaks (2-theta values) as described in Table 3 below, and in particular having peaks at 19.8 in combination with one or more of the peaks selected from the group consisting of 6.8, 16.0, and 22.1; with a tolerance for the diffraction angles of 0.2 degrees.

TABLE 4

X-ray Powder Diffraction Peaks of the Crystalline Example 1B

| Peak | Angle (°2-Theta) +/− 0.2° | Relative Intensity (% of most intense peak) |
| --- | --- | --- |
| 1 | 6.8 | 29.40 |
| 2 | 15.3 | 8.30 |
| 3 | 16.0 | 20.10 |
| 4 | 17.4 | 7.60 |
| 5 | 18.1 | 16.00 |
| 6 | 19.8 | 100.00 |
| 7 | 21.1 | 14.60 |
| 8 | 22.1 | 28.90 |
| 9 | 24.9 | 16.40 |
| 10 | 25.4 | 21.90 |

Alternate Preparation Example 1B

Dissolve 4-{2-[3-(fluoromethyl)azetidin-1-yl]ethoxy}phenyl)(hydroxy)methyl]-3-[2-fluoro-4-(trifluoromethyl)phenyl]quinolin-7-ol, Isomer 1 (63.05 g, 104.7 mmol) in DMSO (1.3 L) under $N_2$ at room temperature. Add in portions cesium carbonate (108 g, 331 mmol) over 5 minutes. Heat the mixture to 60° C. for 15 hours. Cool the mixture to room temperature and dilute with water (2.1 L) and EtOAc (1.3 L). Stir the mixture for 5 minutes and separate. Re-extract the aqueous material with EtOAc (1.3 L) and stir for 5 minutes. Separate and combine the organic extracts, wash with brine, water, and EtOAc. Dry the organic extracts with $MgSO_4$, concentrate, and dry under high vacuum overnight at room temperature to give the title compound as a brown solid (52.69 g, 95.9%). Confirm enantiomeric enrichment of Example 1B by chiral analytical SFC, 98.1% ee, $t_{(R)}$: 2.03 minutes; column: CHIRALCEL® OD-H, 4.6×150 mm; eluting with a mobile phase of 30% MeOH (0.2% IPA) in $CO_2$; column temperature: 40° C.; flow rate: 5 mL/minute; UV detection wavelength: 225 nm.

Example 2A 5-(4-{2-[3-(Fluoromethyl)azetidin-1-yl]ethoxy}phenyl)-7-(trifluoromethyl)-5H-[1]benzopyrano[4,3-c]quinolin-2-ol, Isomer 1 and Example 2B 5-(4-{2-[3-(Fluoromethyl)azetidin-1-yl]ethoxy}phenyl)-7-(trifluoromethyl)-5H-[1]benzopyrano[4,3-c]quinolin-2-ol, Isomer 2

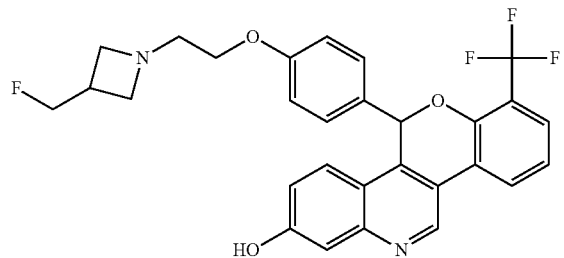 [SMILES: Oc1ccc2c3c(cnc2c1)-c1cccc(C(F)(F)F)c1OC3c1ccc(OCCN2CC(CF)C2)cc1]

Separate the two enantiomers of 5-(4-{2-[3-(fluoromethyl)azetidin-1-yl]ethoxy}phenyl)-7-(trifluoromethyl)-5H-[1]benzopyrano[4,3-c]quinolin-2-ol by chiral SFC with the following conditions: Column: CHIRALPAK® IC, 21×250 cm; eluting with a mobile phase of 30% iPrOH (with 0.2% IPA) in $CO_2$; column temperature: 40° C.; flow rate: 70 g/minute; UV detection wavelength: 225 nm to give Example 2A as the first eluting enantiomer (Isomer 1). ES/MS (m/z): 525.1 (M+H). Confirm enantiomeric enrichment of Isomer 1 by chiral analytical SFC, >99% ee, $t_{(R)}$: 1.56 minutes; column: CHIRALPAK® IC, 4.6×150 mm; eluting with a mobile phase of 30% iPrOH (0.2% IPA) in CO$_2$; column temperature: 40° C.; flow rate: 5 mL/minute; UV detection wavelength: 225 nm. Isolate the title compound of Example 2B to give the second eluting enantiomer (Isomer 2). ES/MS (m/z): 525.2 (M+H). Confirm enantiomeric enrichment of Isomer 2 by chiral analytical SFC, 98% ee, t$_{(R)}$: 2.33 minutes; column: CHIRALPAK® IC, 4.6×150 mm; eluting with a mobile phase of 30% iPrOH (0.2% IPA) in CO$_2$; column temperature: 40° C.; flow rate: 5 mL/minute; UV detection wavelength: 225 nm.

Example 3A

8-Chloro-5-(4-{2-[3-(fluoromethyl)azetidin-1-yl]ethoxy}phenyl)-5H-[1]benzopyrano[4,3-c]quinolin-2-ol, Isomer 1 and Example 3B 8-Chloro-5-(4-{2-[3-(fluoromethyl)azetidin-1-yl]ethoxy}phenyl)-5H-[1]benzopyrano[4,3-c]quinolin-2-ol, Isomer 2

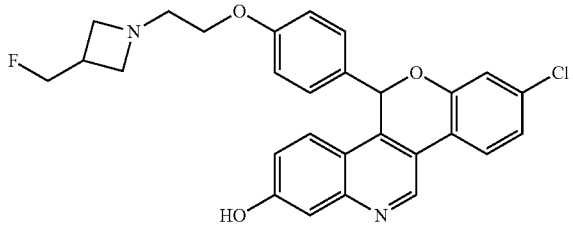 [SMILES: Oc1ccc2c3c(cnc2c1)-c1ccc(Cl)cc1OC3c1ccc(OCCN2CC(CF)C2)cc1]

Separate the two enantiomers of 8-chloro-5-(4-{2-[3-(fluoromethyl)azetidin-1-yl]ethoxy}phenyl)-5H-[1]benzopyrano[4,3-c]quinolin-2-ol by chiral SFC with the following conditions: Column: CHIRALCEL® OD-H, 21×250 cm; eluting with a mobile phase of 35% MeOH (with 0.2% IPA) in CO$_2$; column temperature: 40° C.; flow rate: 80 g/minute; UV detection wavelength: 225 nm to give Example 3A as the first eluting enantiomer (Isomer 1). ES/MS (m/z): 491.0 (M+H). Confirm enantiomeric enrichment of Isomer 1 by chiral analytical SFC, >99% ee, t$_{(R)}$: 1.55 minutes; column: CHIRALCEL® OD-H, 4.6×150 mm; eluting with a mobile phase of 35% MeOH (0.2% IPA) in CO$_2$; column temperature: 40° C.; flow rate: 5 mL/minute; UV detection wavelength: 225 nm. Isolate the title compound of Example 3B to give the second eluting enantiomer (Isomer 2). ES/MS (m/z): 491.0 (M+H). Confirm enantiomeric enrichment of Isomer 2 by chiral analytical SFC, >99% ee, t$_{(R)}$: 2.26 minutes; column: CHIRALCEL® OD-H, 4.6×150 mm; eluting with a mobile phase of 35% MeOH (0.2% IPA) in CO$_2$; column temperature: 40° C.; flow rate: 5 mL/minute; UV detection wavelength: 225 nm.

Example 4A

7-Chloro-5-(4-{2-[3-(fluoromethyl)azetidin-1-yl]ethoxy}phenyl)-5H-[1]benzopyrano[4,3-c]quinolin-2-ol, Isomer 1 and Example 4B 7-Chloro-5-(4-{2-[3-(fluoromethyl)azetidin-1-yl]ethoxy}phenyl)-5H-[1]benzopyrano[4,3-c]quinolin-2-ol, Isomer 2

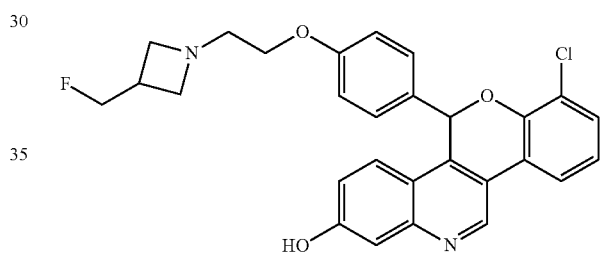

Separate the two enantiomers of 7-chloro-5-(4-{2-[3-(fluoromethyl)azetidin-1-yl]ethoxy}phenyl)-5H-[1]benzopyrano[4,3-c]quinolin-2-ol by chiral SFC with the following conditions: Column: CHIRALCEL® OD-H, 21×250 cm; eluting with a mobile phase of 35% MeOH (with 0.2% IPA) in CO$_2$; column temperature: 40° C.; flow rate: 80 g/minute; UV detection wavelength: 225 nm to give Example 4A as the first eluting enantiomer (Isomer 1). ES/MS (m/z): 491.0 (M+H). Confirm enantiomeric enrichment of Isomer 1 by chiral analytical SFC, >99% ee, t$_{(R)}$: 1.71 minutes; column: CHIRALCEL® OD-H, 4.6×150 mm; eluting with a mobile phase of 35% MeOH (0.2% IPA) in CO$_2$; column temperature: 40° C.; flow rate: 5 mL/minute; UV detection wavelength: 225 nm. Isolate the title compound of Example 4B to give the second eluting enantiomer (Isomer 2). ES/MS (m/z): 491.0 (M+H). Confirm enantiomeric enrichment of Isomer 2 by chiral analytical SFC, >99% ee, t$_{(R)}$: 2.38 minutes; column: CHIRALCEL® OD-H, 4.6×150 mm; eluting with a mobile phase of 35% MeOH (0.2% IPA) in CO$_2$; column temperature: 40° C.; flow rate: 5 mL/minute; UV detection wavelength: 225 nm.

Example 5A

8-Fluoro-5-(4-{2-[3-(fluoromethyl)azetidin-1-yl]ethoxy}phenyl)-5H-[1]benzopyrano[4,3-c]quinolin-2-ol, Isomer 1 and

Example 5B

8-Fluoro-5-(4-{2-[3-(fluoromethyl)azetidin-1-yl]ethoxy}phenyl)-5H-[1]benzopyrano[4,3-c]quinolin-2-ol, Isomer 2

Example 6A

7-Fluoro-5-(4-{2-[3-(fluoromethyl)azetidin-1-yl]ethoxy}phenyl)-5H-[1]benzopyrano[4,3-c]quinolin-2-ol, Isomer 1 and

Example 6B

7-Fluoro-5-(4-{2-[3-(fluoromethyl)azetidin-1-yl]ethoxy}phenyl)-5H-[1]benzopyrano[4,3-c]quinolin-2-ol, Isomer 2

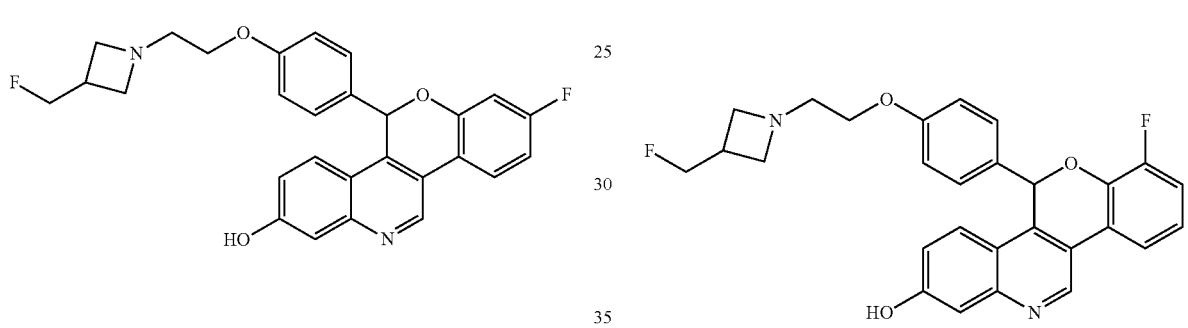

Separate the two enantiomers of 8-fluoro-5-(4-{2-[3-(fluoromethyl)azetidin-1-yl]ethoxy}phenyl)-5H-[1]benzopyrano[4,3-c]quinolin-2-ol by chiral SFC with the following conditions: Column: CHIRALCEL® OD-H, 21×250 cm; eluting with a mobile phase of 30% MeOH (with 0.2% IPA) in $CO_2$; column temperature: 40° C.; flow rate: 80 g/minute; UV detection wavelength: 225 nm to give Example 5A as the first eluting enantiomer (Isomer 1). ES/MS (m/z): 475.0 (M+H). Confirm enantiomeric enrichment of Isomer 1 by chiral analytical SFC, >99% ee, $t_{(R)}$: 1.56 minutes; column: CHIRALCEL® OD-H, 4.6×150 mm; eluting with a mobile phase of 30% MeOH (0.2% IPA) in $CO_2$; column temperature: 40° C.; flow rate: 5 mL/minute; UV detection wavelength: 225 nm. Isolate the title compound of Example 5B to give the second eluting enantiomer (Isomer 2). ES/MS (m/z): 475.0 (M+H). Confirm enantiomeric enrichment of Isomer 2 by chiral analytical SFC, >99% ee, $t_{(R)}$: 2.29 minutes; column: CHIRALCEL® OD-H, 4.6×150 mm; eluting with a mobile phase of 30% MeOH (0.2% IPA) in $CO_2$; column temperature: 40° C.; flow rate: 5 mL/minute; UV detection wavelength: 225 nm.

Separate the two enantiomers of 7-fluoro-5-(4-{2-[3-(fluoromethyl)azetidin-1-yl]ethoxy}phenyl)-5H-[1]benzopyrano[4,3-c]quinolin-2-ol by chiral SFC with the following conditions: Column: CHIRALCEL® OD-H, 21×250 cm; eluting with a mobile phase of 35% MeOH (with 0.2% IPA) in $CO_2$; column temperature: 40° C.; flow rate: 80 g/minute; UV detection wavelength: 225 nm to give Example 6A as the first eluting enantiomer (Isomer 1). ES/MS (m/z): 475.0 (M+H). Confirm enantiomeric enrichment of Isomer 1 by chiral analytical SFC, >99% ee, $t_{(R)}$: 1.32 minutes; column: CHIRALCEL® OD-H, 4.6×150 mm; eluting with a mobile phase of 35% MeOH (0.2% IPA) in $CO_2$; column temperature: 40° C.; flow rate: 5 mL/minute; UV detection wavelength: 225 nm. Isolate the title compound of Example 6B to give the second eluting enantiomer (Isomer 2). ES/MS (m/z): 475.0 (M+H). Confirm enantiomeric enrichment of Isomer 2 by chiral analytical SFC, >99% ee, $t_{(R)}$: 1.95 minutes; column: CHIRALCEL® OD-H, 4.6×150 mm; eluting with a mobile phase of 35% MeOH (0.2% IPA) in $CO_2$; column temperature: 40° C.; flow rate: 5 mL/minute; UV detection wavelength: 225 nm.

Example 8A 5-(4-{2-[3-(Fluoromethyl)azetidin-1-yl]
ethoxy}phenyl)-7-methyl-5H-[1]benzopyrano[4,3-c]
quinolin-2-ol, Isomer 1 and

Example 8B 5-(4-{2-[3-(Fluoromethyl)azetidin-1-yl]
ethoxy}phenyl)-7-methyl-5H-[1]benzopyrano[4,3-c]
quinolin-2-ol, Isomer 2

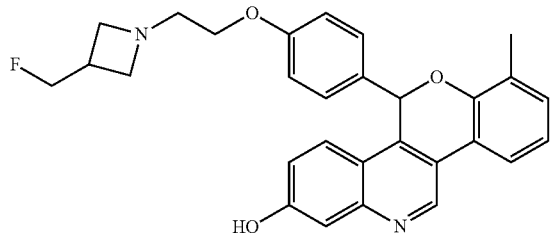 [SMILES: Cc1cccc2c1OC(c1ccc(OCCN3CC(CF)C3)cc1)c1c-2cnc2cc(O)ccc12]

Separate the two enantiomers of 5-(4-{2-[3-(fluoromethyl)azetidin-1-yl]ethoxy}phenyl)-7-methyl-5H-[1]benzopyrano[4,3-c]quinolin-2-ol by chiral SFC with the following conditions: Column: CHIRALCEL® OD-H, 21×250 cm; eluting with a mobile phase of 30% iPrOH (with 0.2% IPA) in $CO_2$; column temperature: 40° C.; flow rate: 80 g/minute; UV detection wavelength: 265 nm to give Example 8A as the first eluting enantiomer (Isomer 1). ES/MS (m/z): 471.2 (M+H). Confirm enantiomeric enrichment of Isomer 1 by chiral analytical SFC, >99% ee, $t_{(R)}$: 1.47 minutes; column: CHIRALCEL® OD-H, 4.6×150 mm; eluting with a mobile phase of 30% iPrOH (0.2% IPA) in $CO_2$; column temperature: 40° C.; flow rate: 5 mL/minute; UV detection wavelength: 225 nm. Isolate the title compound of Example 8B to give the second eluting enantiomer (Isomer 2). ES/MS (m/z): 471.2 (M+H). Confirm enantiomeric enrichment of Isomer 2 by chiral analytical SFC, >99% ee, $t_{(R)}$: 2.05 minutes; column: CHIRALCEL® OD-H, 4.6×150 mm; eluting with a mobile phase of 30% iPrOH (0.2% IPA) in $CO_2$; column temperature: 40° C.; flow rate: 5 mL/minute; UV detection wavelength: 225 nm.

Example 9

5-(4-{2-[3-(Fluoromethyl)azetidin-1-yl]
ethoxy}phenyl)-8-(trifluoromethyl)-5H-[1]benzopyrano[4,3-c]quinolin-2-ol, Isomer 2, benzenesulfonic
acid

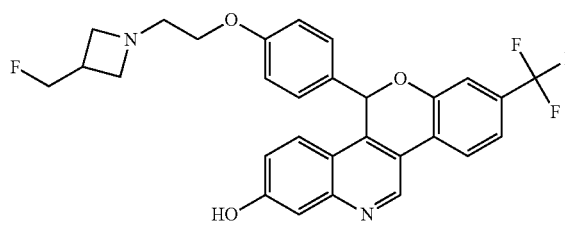

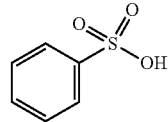

Heat a slurry of 5-(4-{2-[3-(fluoromethyl)azetidin-1-yl]ethoxy}phenyl)-8-(trifluoromethyl)-5H-[1]benzopyrano[4,3-c]quinolin-2-ol, Isomer 2 (Example 1B) (100 mg, 0.19 mmol) in ACN (3 mL) at 50° C. Add a solution of benzenesulfonic acid monohydrate (40 mg, 0.23 mmol) in ACN (1 mL). Heat the clear yellow solution for 10 minutes at 50° C. Discontinue heating, allow the reaction mixture to cool to room temperature, and stir the mixture overnight. Add toluene (2 mL) and stir the reaction mixture 2 hours. Filter the solution, collect the resulting solid and wash the solid with ACN (1 mL). Dry the solid under vacuum to give the title compound (74 mg, 55%).

Alternate Preparation Example 9

Heat a slurry of 5-(4-{2-[3-(fluoromethyl)azetidin-1-yl]ethoxy}phenyl)-8-(trifluoromethyl)-5H-[1]benzopyrano[4,3-c]quinolin-2-ol, Isomer 2 (Example 1B) (124.1 mg, 0.24 mmol) in MEK (4 mL) at 50° C. Add a solution of benzenesulfonic acid monohydrate (50 mg, 0.28 mmol) dissolved in MEK (1 mL). Discontinue heating, allow the reaction mixture to cool to room temperature, and stir the mixture over a weekend. Concentrate under a $N_2$ stream. Add MEK (1 mL) and slurry to give a yellow crystalline solid. Collect the solid, wash with MEK, and dry under room temperature vacuum to give the title compound (78.8 mg, 48%).

XRD, Example 9

Complete XRD as described for Example 1B. Characterize a prepared sample of -(4-{2-[3-(fluoromethyl)azetidin-1-yl]ethoxy}phenyl)-8-(trifluoromethyl)-5H-[1]benzopyrano[4,3-c]quinolin-2-ol, Isomer 2, benzenesulfonic acid by an XRD pattern using CuKa radiation as having diffraction peaks (2-theta values) as described in Table 4 below, and in particular having peaks at 20.5 in combination with one or more of the peaks selected from the group consisting of 12.3, 22.2, and 23.1; with a tolerance for the diffraction angles of 0.2 degrees.

TABLE 5

X-ray Powder Diffraction Peaks of the Crystalline Example 9

| Peak | Angle (°2-Theta) +/− 0.2° | Relative Intensity (% of most intense peak) |
|---|---|---|
| 1 | 7.6 | 27.10 |
| 2 | 10.6 | 34.50 |
| 3 | 12.3 | 42.10 |
| 4 | 12.6 | 32.30 |
| 5 | 17.7 | 32.80 |
| 6 | 19.2 | 26.70 |
| 7 | 20.5 | 100.00 |
| 8 | 22.2 | 45.50 |
| 9 | 23.1 | 36.30 |
| 10 | 24.2 | 29.80 |

Example 10

Crystalline 5-(4-{2-[3-(Fluoromethyl)azetidin-1-yl]ethoxy}phenyl)-8-(trifluoromethyl)-5H-[1]benzopyrano[4,3-c]quinolin-2-ol, 4-methylbenzenesulfonic acid, Isomer 2

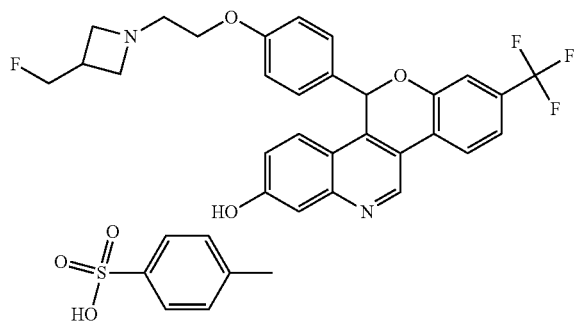

Add together 5-(4-{2-[3-(fluoromethyl)azetidin-1-yl]ethoxy}phenyl)-8-(trifluoromethyl)-5H-[1]benzopyrano[4,3-c]quinolin-2-ol, Isomer 2 (Example 1B) (204.2 g, 389 mmol) and EtOAc (5 L) and stir at 60° C. followed by the addition of MeOH (200 mL) at 60° C. to give a clear brown solution. Add the title product (11.48 g) to seed the solution followed by the addition of a pre-mixed solution of 4-methylbenzenesulfonic acid; hydrate (81.4 g, 428 mmol) in EtOAc (800 mL) to give a yellow suspension. Stir the suspension for 30 minutes at 50° C. Concentrate the suspension to ½ volume. Cool the solution at room temperature for 1 hour, filter, collect the solid, and wash the solid with EtOAc. Dry the solid under vacuum at 30° C. over a weekend to give the title compound (239 g, 343 mmol). To further purify the material, add the title compound (229 g, 328.7 mmol) and 2-propanol (4.6 L) together and heat to 60° C. for 2 hours. Cool to room temperature for 30 minutes. Filter the solid and wash with iPrOH (100 mL). Dry the solid under a stream of $N_2$ overnight to give the title compound (174.4 g, 76.2%). Combine various lots of the title compound prepared essentially in the same manner and add heptane (2 L). Stir the suspension for 30 minutes, filter the solid, and wash with heptane (300 mL). Dry the collected solid under a stream of $N_2$ overnight to give the title compound (199.7 g, 99.5%).

XRD, Example 10

Complete the XRD as described for Example 1B. A prepared sample of 5-(4-{2-[3-(fluoromethyl)azetidin-1-yl]ethoxy}phenyl)-8-(trifluoromethyl)-5H-[1]benzopyrano[4,3-c]quinolin-2-ol, 4-methylbenzenesulfonic acid, Isomer 2 (Example 10) is characterized by an XRD pattern using CuKa radiation as having diffraction peaks (2-theta values) as described in Table 5 below, and in particular having peaks at 20.1 in combination with one or more of the peaks selected from the group consisting of 12.8, 19.5, and 22.8; with a tolerance for the diffraction angles of 0.2 degrees.

TABLE 6

X-ray Powder Diffraction Peaks of the Crystalline Ex 10

| Peak | Angle (°2-Theta) +/− 0.2° | Relative Intensity (% of most intense peak) |
| --- | --- | --- |
| 1 | 7.6 | 25.70 |
| 2 | 12.4 | 27.90 |
| 3 | 12.8 | 36.80 |
| 4 | 18.9 | 26.50 |
| 5 | 19.5 | 56.90 |
| 6 | 20.1 | 100.00 |
| 7 | 20.9 | 41.50 |
| 8 | 21.8 | 40.90 |
| 9 | 22.8 | 39.40 |
| 10 | 25.4 | 29.70 |

Biological Assays

The evidence for a relationship between ER expression and certain cancers is well known in the art.

The results of the following assays demonstrate that the compounds of Formula I, Formula II, and Formula III of the examples are active SERDs and are conceived to be useful in treating cancer.

ERα (Wild Type), ERα (Y537S Mutant) and ERβ Competition Binding Assay

The purpose of the following ER competition binding assays is to determine the affinity of a test compound against ERα (wild type), ERα (Y537S mutant), and ERβ.

Run the competition binding assay in a buffer containing 50 mM HEPES, pH 7.5, 1.5 mM EDTA, 150 mM NaCl, 10% glycerol, 1 mg/mL ovalbumin, and 5 mM DTT, using 0.025 μCi per well $^3$H-estradiol (118 μCi/mmol, 1 mCi/mL), 7.2 ng/well ERα (wild type), or 7.2 ng/well ERα (Y537S mutant) or 7.7 ng/well ERβ receptor. Add the test compound at 10 different concentrations ranging from 10,000 nM to 0.5 nM, and determine nonspecific binding in the presence of 1 μM of 17-β estradiol. Incubate the binding reaction (140 μL) for 4 hours at room temperature, and then add cold dextran-charcoal buffer (70 μL) (containing per 50 mL of assay buffer, 0.75 g of charcoal and 0.25 g of dextran) to each reaction. Mix the plates for 8 minutes on an orbital shaker at 4° C. and then centrifuge at 3000 rpm at 4° C. for 10 minutes. Transfer an aliquot (120 μL) of the mixture to another 96-well, white flat bottom plate (Costar) and add Perkin Elmer Optiphase Supermix scintillation fluid (175 μL) to each well. Seal the plates and shake vigorously on an orbital shaker. After an incubation of 2.5 hours, read the plates in a Wallac Microbeta counter. Calculate the $IC_{50}$ using a 4-parameter logistic curve fit and calculate % inhibition at 10 μM. Convert the $IC_{50}$ values for the compound to $K_i$ using Cheng-Prusoff equation. The results of this assay demonstrate Examples 1, 1A, and 1B (and others) bind to recombinant ERα wild type and ERα mutant (Y537S) as shown in Table 7 below and Example 1B was also determined to bind to ERβ with a $K_i$ (nM) ERβ competition of 0.11±0.07, n=3.

TABLE 7

ERα (wild type), ERα (Y537S mutant) and ERβ competition binding results

| Example # | $K_i$ (nM) ERα (wild type) | $K_i$ (nM) ERα (Y537S mutant) |
|---|---|---|
| 1 | 0.87 | 5.80 |
| 1A | 12.45 ± 9.32, n = 3 | 57.18 ± 39.13, n = 3 |
| 1B | 0.31 ± 0.38, n = 5 | 2.79 ± 3.00, n = 5 |
| 2 | 2.17 | 6.78 |
| 2A | 0.65 | 7.92 |
| 2B | 60.4 | 293.6 |
| 3 | 2.36 | 6.69 |
| 3A | 8.11 | 27.23 |
| 3B | 0.59 | 2.79 |
| 4 | 0.64 | 12.11 |
| 4A | 16.78 | 54.97 |
| 4B | 0.34 | 2.34 |
| 5 | 2.82 | 19.47 |
| 5A | 12.54 | 81.15 |
| 5B | 1.30 | 6.56 |
| 6 | 4.14 | 15.77 |
| 6A | 8.53 | 45.99 |
| 6B | 1.13 | 5.71 |
| 7 | 1.55 | 8.55 |
| 8 | 3.20 | 11.4 |
| 8A | 9.33 | 66.94 |
| 8B | 0.94 | 5.44 |

Of the exemplified compounds tested, the Ki for ERα wildtype ranged from about 0.300 nM to about 65 nM. The Ki for ERα Y537S mutant ranged from about 2 nM to 300 nM. The results of this assay demonstrate the binding affinity and potency of the exemplified compounds against ERα wild type, mutant (ESR1 Y537S) and ERβ proteins.

ERα Degradation Assay in MCF7 Cells

The purpose of the following ERα degradation assay is to measure the degradation of ERα by a test compound in an ERα positive breast cancer cell line such as MCF7.

Culture MCF7 (purchased from ATCC HTB-22) cells in DMEM media supplemented with 10% FBS, 0.01 mg/mL human insulin 1 and 1% penicillin/streptomycin antibiotics and plate in 384-well flat-bottom plates at a density of 4,000 cells per well in phenol red free DMEM media (20 μL) containing 10% charcoal stripped FBS. Incubate the cells overnight in a cell culture incubator (5% $CO_2$, 95% relative humidity and 37° C.) and allow the cells to attach to the plate. The following day dose the cells with the test compound. Use an Echo 555 acoustic dispenser to prepare test compound serial dilutions (1:3) in a range from 6 μM to 0.0003 μM. Dose the cells with the addition of 5 μL from the serial dilution plate to the cell plate producing a final DMSO concentration of 0.2% with a final test compound concentration dose range between 2 and 0.0001 μM. For the maximum point, use media containing 0.2% of DMSO and for the minimum point, use fulvestrant diluted at 2 μM final concentrations in the growth media containing 0.2% DMSO. After dosing with the test compound, incubate the cell plates at 37° C. and 5% $CO_2$ for 24 hours. Fix the cells by adding 14% para-formaldehyde (10 μL) for 30 minutes at room temperature. Wash the cells once with PBS (20 μL) and incubate with PBS (20 μL) containing 0.5% (v/v) TWEEN® 20 for 1 hour. Wash the cells with PBS containing 0.05% TWEEN® 20 (2×) and block with 3% BSA in PBS containing 0.05% TWEEN® 20 and 0.1% TRITON™ X-100 (20 μL/well) for 1 hour at room temperature. Add 1:500 Primary antibody (20 μL) (ERα (Clone SP1) monoclonal rabbit antibody #RM-9101-S, Thermo Scientific) dilution in 1% BSA in PBS containing 0.05% TWEEN® 20 per well, seal the plates and incubate overnight at 4° C. The following day wash the cells with PBS containing 0.05% TWEEN® 20 (2×) and incubate with secondary antibody (20 μL/well) (1:1000 dilution, Goat anti-rabbit IgM ALEXA FLUOR™ 488) in PBS 1% BSA for 105 minutes at room temperature. After washing plates with PBS (2×20 μL), add RNase (Sigma) (20 μL of 50 g/mL) and 1:1000 propidium iodide dilution in PBS per well (20 μL). Seal the plates and incubate 1 hour at room temperature on the bench (preserved from light). Scan the plates with ACUMEN EXPLORER™ [Laser-scanning fluorescence microplate cytometer manufactured by TTP LABTECH LTD] to measure ERα. Image analysis is based on cellular fluorescent signals for identifying positive cells. Identify ER positive cells by mean intensity. Use total intensity at 575-640 nm from propidium iodide/DNA to identify individual cells. Assay output is % ER positive cells. Determine the $IC_{50}$ by curve fitting to a four parameter logistic for each output using GENE DATA™. The results of this assay demonstrate potent degradation of ERα induced by the compounds of Formula I, Formula II, and Formula III as described herein in MCF7 breast cancer cells. The Relative $IC_{50}$ values for Examples 1, 1A, and 1B are shown in Table 8.

TABLE 8

ERα degradation assay in MCF7 cells

| Example # | Relative $IC_{50}$ (μM) |
|---|---|
| 1 | 0.003405 ± 0.001086, n = 3 |
| 1A | 0.3940 ± 0.1941, n = 4 |
| 1B | 0.003088 ± 0.001523, n = 19 |
| 2 | 0.05220 ± 0.006508, n = 2 |
| 2A | 0.05125 ± 0.01626, n = 2 |
| 2B | >2 |
| 3 | 0.03347 ± 0.007830, n = 3 |
| 3A | 0.3905 |
| 3B | 0.008664 |
| 4 | 0.02241 ± 0.0003553, n = 3 |
| 4A | 0.4998 |
| 4B | 0.006892 |
| 5 | 0.03653 + 0.03738, n = 2 |
| 5A | 0.5221 |
| 5B | 0.009493 ± 0.001103, n = 2 |
| 6 | 0.05086 ± 0.006889, n = 3 |
| 6A | 0.1753 |
| 6B | 0.009132 |
| 7 | 0.07879 ± 0.007379, n = 2 |
| 8 | 0.01738 ± 0.008752, n = 2 |
| 8A | 0.2341 |
| 8B | 0.009617 ± 0.005198, n = 2 |
| 10 | 0.004216 ± 0.001619, n = 5 |

Specifically, the results in Table 7 show potent degradation of ERα by the compound of Example 1 in MCF7 breast cancer cells. Of the exemplified compounds tested, the relative $IC_{50}$ ranged from 0.003 to >2 μM indicating that all but Example 2B showed activity at the concentration tested. The results of this assay demonstrate that the compound of Formula (I) is a SERD with potent ERα degradation activity in cells.

PRα Induction Assay in MCF7 Cells

The purpose of the following PRα induction assay is to determine whether a test compound has agonistic activity against ERα receptor (an agonist would be expected to activate the receptor).

Culture MCF7 (purchased from ATCC HTB-22) in DMEM media supplemented with 10% FBS, 0.01 mg/mL human insulin 1 and 1% penicillin/streptomycin antibiotics and plate the cells (prior to becoming 70% confluent) in 384-well flat-bottom plates at a density of 4,000 cells per well in 20 μL volume in DMEM phenol red free media containing 10% FBS (charcoal stripped). Incubate the cells overnight in a cell culture incubator (5% $CO_2$, 95% relative humidity at 37° C.) and allow the cells to attach to the plate. The following day, dose the cells with test compound. Use an Echo 555 acoustic dispenser to prepare compound serial dilutions (1:3) in a range from 6 μM to 0.0003 μM. Dose the cells with the addition of the test compound (5 μL) from the serial dilution plate to the cell plate producing a final DMSO concentration of 0.2% with a final concentration of the test compound dose range between 2 and 0.0001 μM. For the maximum point use media containing 0.2% of DMSO and for the minimum point, use fulvestrant diluted at 2 M final concentrations in the growth media containing 0.2% DMSO. After dosing with the test compound, incubate the cell plates at 37° C. and 5% $CO_2$ for 24 hours. Fix the cells by adding 14% para-formaldehyde (10 μL) for 30 minutes at room temperature. Wash cells once with PBS (20 μL) and incubate with PBS (20 μL) containing 0.5% (v/v) TWEEN® 20 for 1 hour. Wash cells twice with PBS (20 μL) containing 0.05% TWEEN® 20 and block with 3% BSA in PBS containing 0.05% TWEEN® 20 and 0.1% TRITON™ X-100 (20 μL/well) for 1 hour at room temperature. Add 1:500 primary antibody (20 μL) (PR monoclonal mouse anti-human antibody, clone PgR 636 Dako, M3569) dilution in 1% BSA/PBS with 0.05 TWEEN® 20 per well, seal the plates and incubate overnight at 4° C.

The following day, wash cells with PBS 0.05% TWEEN® 20 (2×20 μL) and incubate with secondary antibody (20 μL/well) (1:1000 dilution, Goat anti-rabbit IgM ALEXA FLUOR™ 488) in PBS 1% BSA for 105 minutes at room temperature. After washing with PBS (2×20 μL), add RNase (20 μL of 50 g/mL) (Sigma) and 1:1000 propidium iodide dilution in PBS per well. Seal plates and incubate 1 hour at room temperature on the bench (preserved from light). Scan plates with ACUMEN EXPLORER™ [Laser-scanning fluorescence microplate cytometer manufactured by TTP LABTECH LTD] to measure PRα. Image analysis is based on cellular fluorescent signals for identifying positive cells. Identify PR positive cells by mean intensity. Use total intensity at 575-640 nm from propidium iodide/DNA to identify individual cells. Assay output is % PR positive cells. Determine the $IC_{50}$ by curve fitting to a four parameter logistic for each output using GENE DATA™. The results of this assay demonstrate no significant agonistic activity of Examples 1, 1A, and 1B in MCF7 breast cancer cells. For the compounds tested, the Relative $IC_{50}$s in this assay are >2 μM. The results of this assay demonstrate no significant agonistic activity of the exemplified compounds tested in MCF7 breast cancer cells. These results also demonstrate that the exemplified compounds tested are antagonists of ERα in MCF7 breast cancer cells (i.e., they have SERD activity).

PRα Inhibition (ERα Functional Antagonism) Cell Assay in MCF7-ESR1 Y537N 682 CRISPR Cells The purpose of the following PRα inhibition (ERα functional antagonism) cell assay is to determine the antagonistic activity of a test compound against the Y537N mutant ERα receptor. An antagonist in this assay is expected to block the function of the ERα receptor. PRα is a downstream transcriptional target of ERα and hence an antagonist of ERα is expected to inhibit the expression of PRα.

Culture MCF7-ESR1 Y537N-682 (generated by CRISPR/Cas9 gene editing of ESR1 gene in MCF7 cells, clone #682) in DMEM media supplemented with 10% FBS and 1% penicillin/streptomycin antibiotics and plate the cells (prior to becoming 70% confluent) in 384-well flat-bottom plates at a density of 4,000 cells per well in DMEM phenol red free media 10% FBS (20 μL volume) (charcoal stripped). Incubate the cells overnight in a cell culture incubator (5% $CO_2$, 95% relative humidity and 37° C.) and allow the cells to attach to the plate. The following day dose the cells with the test compound. Use an Echo 555 acoustic dispenser to prepare compound serial dilutions (1:3) in a range from 6 μM to 0.0003 M. Dose the cells with the addition of 5 μL from the serial dilution plate to the cell plate producing a final DMSO concentration of 0.2% with a final test compound concentration dose range between 2 and 0.0001 μM. For the maximum point use media containing 0.2% of DMSO and for the minimum point, use fulvestrant diluted at 2 μM final concentrations in the growth media containing 0.2% DMSO. After dosing with test compound, incubate the cell plates at 37° C. and 5% $CO_2$ for 72 hours. Fix the cells by adding 14% para-formaldehyde (10 μL) for 30 minutes at room temperature. Wash the cells with PBS (1×20 μL) and incubate with PBS (20 μL) of containing 0.5% (v/v) TWEEN® 20 for 1 hour. Wash the cells with PBS (2×20 μL), 0.05% TWEEN® 20, and block with 3% BSA/PBS 0.05% TWEEN® 20, 0.1% TRITON™ X-100 (20 μL/well) for 1 hour at room temperature. Add 1:500 primary antibody (20 μL) (PR monoclonal mouse anti-human antibody, clone PgR 636 Dako, M3569) dilution in 1% BSA/PBS 0.05 TWEEN® 20 per well, seal the plates and incubate overnight at 4° C.

The following day, wash the cells with PBS 0.05% @ (2×20 μL) and incubate with secondary antibody (20 μL/well) (1:1000 dilution, Goat anti-rabbit IgM ALEXA FLUOR™ 488) in PBS 1% BSA for 105 minutes at room temperature. After washing with PBS (220 μL), add RNase (20 μL of 50 μg/mL) (Sigma) and 1:1000 propidium iodide dilution in PBS per well. Seal the plates and incubate 1 hour at room temperature on the bench (preserved from light). Scan the plates with ACUMEN EXPLORER™ [Laser-scanning fluorescence microplate cytometer manufactured by TTP LABTECH LTD] to measure PRα. Image analysis is based on cellular fluorescent signals for identifying positive cells. Identify PR positive cells by mean intensity. Use total intensity at 575-640 nm from propidium iodide/DNA to identify individual cells. Assay output is % PR positive cells. Determine the $IC_{50}$ by curve fitting to a four parameter logistic for each output using GENE DATA™.

The results of this assay demonstrate potent inhibition of PRα and functional antagonism by Examples 1, 1A, and 1B in MCF7 (ESR1 Y537N, heterozygous mutant) breast cancer cells. The Relative $IC_{50}$ of Examples 1, 1A, and 1B (and others) in this assay are shown in Table 9 below. The Relative $IC_{50}$s of the exemplified compounds tested range from about 0.0118 to >1.6 μM indicating the exemplified compounds are potent antagonist of ERα mutant (Y537N) and potent inhibitors of ERα mediated transcription except example 2B 1.6 μM). PRα (PGR) is also a transcriptional target of ERα and the results from this assay demonstrate potent inhibition of ERα-mediated transcription of PRα.

TABLE 9

PRα inhibition (ERα functional antagonism) cell assay in MCF7 Y537N 682 CRISPR cells

| Example # | Relative IC$_{50}$ (μM) |
|---|---|
| 1 | 0.01679 ± 0.00003, n = 2 |
| 1A | 1.20 ± 0.29, n = 2 |
| 1B | 0.0130 ± 0.0059, n = 14 |
| 2 | 0.01451 ± 0.002619, n = 2 |
| 2A | 0.02494 ± 0.007386, n = 3 |
| 2B | 1.639 ± 0.2228, n = 3 |
| 3 | 0.07717 ± 0.01154, n = 2 |
| 3A | 0.6117 |
| 3B | 0.016 |
| 4 | 0.03854 + 0.003865, n = 2 |
| 4A | 0.5052 |
| 4B | 0.01181 |
| 5 | 0.06614 ± 0.01551, n = 2 |
| 5A | 0.3945 |
| 5B | 0.01822 + 0.009815, n = 2 |
| 6 | 0.06319 ± 0.01609, n = 2 |
| 6A | 0.2364 |
| 6B | 0.0136 |
| 7 | 0.1271 |
| 8 | 0.04124 + 0.006572, n = 2 |
| 8A | 0.4335 + 0.1946, n = 3 |
| 8B | 0.008926 ± 0.003828, n = 3 |
| 10 | 0.007936 ± 0.003163, n = 3 |

TABLE 10

PRα inhibition (ERα functional antagonism) cell assay in MCF7 cells

| Example # | Relative IC$_{50}$ (μM) |
|---|---|
| 1 | 0.1283 ± 0.0226, n = 3 |
| 1A | >2.000 |
| 1B | 0.04129 ± 0.03370, n = 16 |
| 2 | 0.1634 |
| 2A | 0.1215 ± 0.05368, n = 2 |
| 2B | >2.000 |
| 3 | 0.07666 ± 0.02101, n = 3 |
| 3A | 0.9274 |
| 3B | 0.03435 |
| 4 | 0.07626 ± 0.1676, n = 3 |
| 4A | 0.8465 |
| 4B | 0.02866 |
| 5 | 0.1180 ± 0.01230, n = 2 |
| 5A | 0.6002 |
| 5B | 0.03203 ± 0.005306, n = 2 |
| 6 | 0.08258 + 0.005682, n = 3 |
| 6A | 0.2528 |
| 6B | 0.02835 |
| 7 | 0.1134 ± 0.02087, n = 2 |
| 8 | 0.06835 ± 0.02273, n = 2 |
| 8A | 0.2058 |
| 8B | 0.04848 ± 0.02944, n = 2 |
| 10 | 0.02633 + 0.004459, n = 3 |

PRα Inhibition (ERα Functional Antagonism) Cell Assay in MCF7 Cells

The purpose of the following PRα inhibition (ERα functional antagonism) cell assay is to determine the antagonistic activity of a test compound against the ERα receptor. An antagonist in this assay is expected to block the function of the ERα receptor. PRα is a downstream transcriptional target of ERα and hence an antagonist of ERα is expected to inhibit the expression of PRα.

Carry out the assay conditions as detailed in the ERα degradation Cell base Acumen assay above, using the MCF7 cell line except that, prior to test compound dispensing, remove the media from the cell plate and pretreat all wells except for the negative control wells (column 24 of the plate) with assay media containing 0.47 nM estradiol for 30 minutes. In this assay, carry out immunostaining for the detection of PRα and scan the plates with ACUMEN EXPLORER™ [Laser-scanning fluorescence microplate cytometer manufactured by TTP LABTECH LTD] to measure PRα. Image analysis is based on cellular fluorescent signals for identifying positive cells. Identify PRα positive cells by mean intensity. Use total intensity at 575-640 from propidium iodide/DNA to identify individual cells. Assay output is % PRα positive cells. Determine the IC$_{50}$ by curve fitting to a four parameter logistic for each output using GENE DATA™. The results of this assay demonstrate potent inhibition of PRα and functional antagonism by Examples 1, 1A, and 1B in MCF7 breast cancer cells. The Relative IC$_{50}$ of Examples 1, 1A, and 1B in this assay are shown in Table 10 below. The Relative IC$_{50}$ of the exemplified compounds range from about 0.029 to >2 μM indicating that all exemplified compounds tested except 1A and 2B, are potent antagonists of ERα wild-type protein and a potent inhibitor of ERα mediated transcription. PRα (PGR) is also a transcriptional target of ERα and the results from this assay demonstrate potent inhibition of ERα-mediated transcription of PRα at the concentration tested.

Cell Proliferation Assay in MCF7 and MCF7-ESR1 Y537N-682

The purpose of the following cell proliferation assays generally is to detect whether a test compound has effects on cell proliferation.

Seed MCF7 (purchased from ATCC HTB-22) cells at a density of 2,000 cells per well in DMEM phenol red free media 10% FBS (20 μL volume) (charcoal stripped) into a clear bottom 384-well cell culture plate. Plate MCF7-ESRY537N-682 (generated by CRISPR/Cas9 gene editing of ESr1 gene in MCF7 cells, clone #682) in DMEM media supplemented with 10% FBS, and 1% penicillin/streptomycin antibiotics at a density of 1000 cells per well. Incubate the plates at 37° C. and 5% CO$_2$. The following day dose the cells with the test compound. Use an Echo 555 acoustic dispenser to prepare test compound serial dilutions (1:3) in a range from 60 μM to 0.003 μM. Dose the cells with the addition of 5 μL from the serial dilution plate to the cell plate, producing a final DMSO concentration of 0.2% with a final test compound concentration dose range between 20 and 0.001 μM. For the maximum point use media containing 0.2% of DMSO and for the minimum point use fulvestrant diluted at 2 μM final concentrations in the growth media containing 0.2% DMSO. After dosing with the test compound, incubate the cell plates at 37° C. and 5% CO$_2$. Seven days after test compound addition, remove the plates from the incubator and add cold EtOH 96% (65 μL) to each well. After 30 minutes, remove the media and add RNase (20 μL of 50 μg/mL) (Sigma) and 1:1000 propidium iodide dilution in PBS per well. Seal the plates and incubate 1 hour at room temperature on the bench (preserved from light). Scan the plates with ACUMEN EXPLORER™ [Laser-scanning fluorescence microplate cytometer manufactured by TTP LABTECH LTD]. The MCF-7 cell line grows forming aggregates, cell number as number of objects may not be able to be used as readout; so the cell number may be evaluated through estimated number of cells (calculated through the area parameter (ratio of total area of the total cells population (a designated range of peak intensity of FL-1 (PI) and the mean area of the single cells population (defined by perimeter)). Determine the $IC_{50}$ by curve fitting to a four parameter logistic for each output using GENE DATA™. The Relative $IC_{50}$ of Examples 1, 1A, and 1B (and others) in MCF7 ESR1 wild type and MCF7-ESR1 Y537N mutant cells are shown in Table 10 below. The results of this assay demonstrate potent anti-proliferative activity and cell growth inhibition by Examples 1, 1A, and 1B (and others) in MCF7 (ESR1 wild type) and MCF7 (ESR1 Y537N mutant) breast cancer cells. The Relative $IC_{50}$ of the exemplified compounds range from about 0.0035 to 1.176 µM in MCF7 ESR1 wild type and 0.014 to 1.86 µM in MCF7 (ESR1 Y537N mutant) breast cancer cells indicating that all exemplified compounds tested demonstrate potent anti-proliferative activity and cell growth inhibition in MCF7 (ESR1 wild type) and MCF7 (ESR1 Y537N mutant) breast cancer cells.

TABLE 11

Cell Proliferation Assay in MCF7 and MCF7-ESR1Y537N-682

| Example # | Relative $IC_{50}$ (µM) MCF7 ESR1 wild type | Relative IC50 (µM) MCF7 ESR1 Y537N mutant cells |
|---|---|---|
| 1 | 0.00768 ± 0.01263, n = 3 | 0.0321 ± 0.0068, n = 2 |
| 1A | 1.18 ± 0.68, n = 4 | 1.86 ± 1.03, n = 4 |
| 1B | 0.00349 ± 0.00225, n = 11 | 0.0167 ± 0.0091, n = 12 |
| 2 | 0.00425 | 0.05113 |
| 2A | 0.00612 | 0.04284 ± 0.002666, n = 2 |
| 2B | 0.4053 | 0.7777 |
| 3 | 0.3287 | 0.02394 |
| 3A | 0.303 | 0.6169 ± 0.1735, n = 3 |
| 3B | 0.008785 | 0.02144 ± 0.008938, n = 3 |
| 4 | 0.02861 | 0.02664 |
| 4A | 0.2862 | 0.5442 ± 0.2181, n = 3 |
| 4B | 0.003496 | 0.01433 ± 0.004925, n = 3 |
| 5 | 0.08009 | 0.07252 + 0.02632, n = 2 |
| 5A | 0.4095 | 0.5167 + 0.09497, n = 3 |
| 5B | 0.007666 | 0.02131 + 0.01300, n = 3 |
| 6 | 0.05128 | 0.02362 |
| 6A | 0.0759 | 0.3234 ± 0.1758, n = 3 |
| 6B | | 0.01539 |
| 7 | 0.01902 | 0.04479 ± 0.01188, n = 2 |
| 8 | 0.04157 | 0.03290 ± 0.003002, n = 2 |
| 8A | 0.1743 | 0.6621 ± 0.1173, n = 2 |
| 8B | 0.005083 | 0.01419 ± 0.01108, n = 2 |
| 10 | 0.004379 | 0.01059 |

In Vivo Target Inhibition (IVTI) Assay (PGR RT-qPCR Assay) in MCF7 Tumors

The purpose of this IVTI assay is to measure the ability of a test compound (SERD) to inhibit PRα gene expression (transcription) downstream of ERα in xenograft tumors implanted in mice.

Implant female NOD SCTD mice (22-25 g) from Envigo RMS, Inc., Madison, Wis. with 5×10e$^6$ MCF7 ER-positive breast cancer cells (ATCC, #HTB-22) subcutaneously in the right flank region in 1:1BSS+MATRIGEL™ solution (200 µL). Implant a 17-β estradiol pellet (0.18 mg/pellet, 90 day release, from Innovative research) subcutaneously 1 day prior to tumor cell implantation. Measure tumor growth and body weight twice per week beginning the seventh day after the implantation. When tumor sizes reach 250-350 mm$^3$, randomize animals and group into groups of five animals. Dose animals with either the test compound at multiple doses in a test compound specific vehicle (1% hydroxyethylcellulose/0.25% TWEEN® 80/0.05% Antifoam in purified water) or vehicle alone orally for 3 days and collect tumors and blood at desired time intervals after last dose. Sacrifice animals using isoflurane anesthesia plus cervical dislocation. Flash freeze tumors and store at −80° C. until processing for RNA isolation and RT-qPCR assay. Collect blood in EDTA tubes, spin down for plasma, and freeze at −80° C. in a 96-well plate. Determine test compound exposures using mass spectrometry.

Pulverize tumors in liquid nitrogen and lyse in 1×RNA lysis buffer (from RNA isolation kits) using Matrix D beads (MP Biomedical, #6913-500) in a FASTPREP-24Tm Cell Disrupter machine (MP Biomedical). Transfer tumor lysates to fresh tubes after spinning at 14000 rpm for 20 minutes at 4° C. Isolate RNA from tumor lysates using PURELINK® RNA Mini Kit (Invitrogen #12183018A) or RNeasy Mini Kit (Qiagen #74104 and #74106). Remove DNA contaminants using PURELINK® DNase Set (Invitrogen #12185010) or RNase-Free DNase Set (Qiagen #79254). Measure isolated RNA concentration by diluting samples in RNase free water and measuring the absorbance at 260 nm on a plate reader (SpectraMax190). Subtract the average 260 nm absorbance measurement of the blank (RNase free water only) from the 260 nm measurements of all other RNA samples. Dilute RNA samples to equal concentrations in RNase free water. Synthesize cDNA from diluted RNA using First-Strand Synthesis System for RT-PCR (Invitrogen, #18080-051). To perform RT-qPCR, first dilute cDNA in RNase free water. Combine 2× Absolute Blue qPCR ROX Mix (Thermo, #AB-4139/A), PGR primer (Thermo, Hs01556702_m1), and diluted cDNA for each reaction in a PCR plate (Applied Biosystems, #4309849). Amplify cDNA by incubating the samples for 2 minutes at 50° C. followed by 15 minutes at 95° C. in the thermocycler (ABI Prism 7900HT Sequence Detection System). Continue to incubate at 95° C. for 15 seconds followed by 50° C. for 60 seconds for a total of 40 cycles. Cycles are normalized to the housekeeping gene and used to calculate % PGR inhibition compared to the vehicle alone. Analyze each sample in duplicate and use average numbers for calculations. Calculate the percent target (PGR) inhibition using Excel and XL Fit.

The results of this assay demonstrates that Example 1B inhibits PRα (PGR) expression in the tumor xenograft model. Example 1B inhibits PRα (PGR) expression by ~78% in the tumor xenograft model for 24 hours with 30 mg/kg dose when administered orally. These results demonstrate significant and sustained inhibition of ERα antagonistic activity and ERα-mediated transcriptional activity in vivo in a tumor xenograft model.

In Vivo Tumor Growth Inhibition Study in ER-Positive (ESR1 Wild Type) Breast Cancer Xenograft Tumor Models Implanted in Mice The purpose of the following xenograft tumor inhibition assay is to measure reduction in tumor volume in response to test compound administration.

Expand human breast cancer cells MCF7 (ATCC #HTB-22) and HCC1428 (ATCC #CRL-2327) in culture, harvest and inject 5×10e$^6$ cells in 1:1 HBSS+MATRIGEL™ solution (200 µL) subcutaneously on to the rear right flank of female NOD SCID mice (22-25 g, Envigo RMS, Inc). Twenty-four hours prior to implantation of cells, implant estrogen pellets (0.18 mg/pellet, 17β estradiol, 90-day release, Innovative Research) subcutaneously. Expand human breast cancer cells T47D (ATCC #HTB-22) in culture, harvest and inject 5×10e$^6$ cells in 1:1 HBSS+MATRIGEL™ solution (200 µL) subcutaneously on to the rear right flank of female NOD SCID mice (22-25 g, Envigo RMS, Inc). Twenty-four hours prior to implantation of cells, implant estrogen pellets (0.38 mg/pellet, 17β estradiol, 90-day release, Innovative Research) subcutaneously. Expand human breast cancer cells ZR-75-1 (ATCC #CRL-1500) in culture, harvest and inject 5×10e$^6$ cells in 1:1 HBSS+MATRIGEL™ solution (200 µL) subcutaneously on to the rear right flank of female NOD SCID mice (22-25 g, Envigo RMS, Inc). Twenty-four hours prior to implantation of cells, animals are administered with 50 µl of estradiol valerate (Delestrogen®) intramascular injection (10 mg/mL) and then once every 14 days for the duration of the study. Measure tumor growth and body weight twice per week beginning the seventh day after the implantation. When tumor sizes reach 250-350 mm$^3$, randomize animals and group into groups of 5 animals. Prepare the test compound, Example 1B in an appropriate vehicle (1% hydroxyethylcellulose/0.25% TWEEN® 80/0.05% Antifoam in purified water) and administer by oral gavage for 28 days, QD. Determine tumor response by tumor volume measurement performed twice a week during the course of treatment. Take the body weight as a general measure of toxicity whenever tumor volume is measured.

The compound of Example 1B is found to have delta T/C % values as provided in Table 12 below. These results indicate that the compound of Example 1B demonstrates good oral bioavailability in mice and significant anti-tumor activity or tumor regressions in ER-positive (ESR1 wild-type) human breast cancer xenograft models.

TABLE 12

In vivo tumor growth inhibition study in ER-positive breast cancer xenograft tumor models implanted in mice

| Tumor Model | Dose (mg/kg) | Delta T/C % or Regression % | p-value |
| --- | --- | --- | --- |
| MCF7 (Breast Cancer Xenograft) | 3 | −26 | 0.001* |
|  | 10 | −46 | <0.001* |
|  | 30 | −36 | <0.001* |
| T47D (Breast Cancer Xenograft) | 3 | 30 | 0.008* |
|  | 10 | −11 | <0.001* |
|  | 30 | −28 | <0.001* |
| ZR-75-1 (Breast Cancer Xenograft) | 3 | 4 | <0.001* |
|  | 10 | 0 | <0.001* |
|  | 30 | 19 | <0.001* |
| HCC1428 (Breast Cancer Xenograft) | 10 | −45 | <0.001* |
|  | 30 | −22 | <0.001* |

Analysis for tumor volume is based on Log 10 and Spatial-Power covariance structure.

*: significant (p<0.05) compared to vehicle control.

Delta T/C % is calculated when the endpoint tumor volume in a treated group is at or above baseline tumor volume. The formula is $100*(T-T_0)/(C-C_0)$, where T and C are mean endpoint tumor volumes in the treated or control group, respectively. $T_0$ and $C_0$ are mean baseline tumor volumes in those groups.

Regression % is calculated when the endpoint volume is below baseline. The formula is $100*(T-T_0)/T_0$, where $T_0$ is the mean baseline tumor volume for the treated group.

Grand mean of all groups from baseline (randomization) at day 32 is used to compute % change of T/C.

In Vivo Tumor Growth Inhibition Study in ESR1 Mutant (Y537S) Breast Cancer PDX Tumor Model (ST941/HI) Implanted in Mice The purpose of the following xenograft tumor inhibition assay is to measure reduction in tumor volume in response to test compound administration in an ESR1 mutant and hormone-independent (HI) breast cancer patient-derived xenograft (PDX) model.

ST941/HI PDX model was derived at and run at South Texas Accelerated Research Therapeutics (San Antonio, Tex.). Tumor fragments were harvested from host animals and implanted into immune-deficient mice (The Jackson Laboratory) and the study was initiated at a mean tumor volume of approximately 125-250 mm$^3$. Prepare the test compound, Example 1B in an appropriate vehicle (1% hydroxyethylcellulose/0.25% TWEEN® 80/0.05% Antifoam in purified water) and administer by oral gavage for 28 days. Determine tumor response by tumor volume measurement performed twice a week during the course of treatment. Take the body weight as a general measure of toxicity whenever tumor volume is measured.

The compound of Example 1B is found to have delta T/C % values as provided in Table 13 below. These results indicate that the compound of Example 1B demonstrates good oral bioavailability in mice and significant anti-tumor activity or tumor regressions in an ESR1 mutant (Y537S) human breast cancer PDX model.

TABLE 13

In vivo tumor growth inhibition study in ESR1 mutant breast cancer PDX tumor model implanted in mice

| Tumor Model | Dose (mg/kg) | Schedule | Delta T/C % or Regression % | p-value |
| --- | --- | --- | --- | --- |
| ST941C/HI (ESR1 Mutant Breast Cancer PDX model) | 3 | QD | 66 | 0.213 |
|  | 10 | QD | 15 | <0.001* |
|  | 30 | QD | 6 | <0.001* |

Analysis for tumor volume is based on Log 10 and Spatial-Power covariance structure.

*: significant (p<0.05) compared to vehicle control.

Delta T/C % is calculated when the endpoint tumor volume in a treated group is at or above baseline tumor volume. The formula is $100*(T-T_0)/(C-C_0)$, where T and C are mean endpoint tumor volumes in the treated or control group, respectively. $T_0$ and $C_0$ are mean baseline tumor volumes in those groups.

Regression % is calculated when the endpoint volume is below baseline. The formula is $100*(T-T_0)/T_0$, where $T_0$ is the mean baseline tumor volume for the treated group.

Grand mean of all groups from baseline (randomization) at day 32 is used to compute % change of T/C.

Combination Studies

Due to tumor heterogeneity and acquired resistance to endocrine therapies, combination therapy has become essential in ER-positive and advanced/metastatic breast cancer treatment for effective therapy or to overcome acquired resistance. We have tested the combination effect of Example 1B with CDK4/6 inhibitor abemaciclib, mTOR inhibitor everolimus, PIK3CA inhibitor alpelisib and PI3K/mTOR inhibitor 8-[5-(1-hydroxy-1-methylethyl)pyridin-3-yl]-1-[(2S)-2-methoxypropyl]-3-methyl-1,3-dihydro-2H-imidazo[4,5-c]quinolin-2-one ("Compound A") in five ER-positive breast cancer cell lines in vitro.

Cell Viability Assay for Combination Studies

Seed cell at the density shown in Table 14 below in 20 µL volume of the media described in the table into a clear bottom 384-well cell culture plate.

TABLE 14

Cell viability assay cell line information

| Cell Line | Seeding density | Commercial reference | Cuture Medium | Fixation time (hours) |
|---|---|---|---|---|
| T-47D | 1000 | ATCC HTB-133 | RMPI 10% FBS 1% P/S, 0.008 mg/mL Bovine Insulin | 72 |
| MCF-7 | 1000 | ATCC HTB-22 | DMEM 10% FBS 1% P/S 0.01 mg/mL human insulin | 96 |
| EFM-19 | 3000 | ACC 231 | RMPI 10% FBS 1% P/S | 144 |
| ZR-75-1 | 1000 | ATCC CRL-1500 | RMPI 10% FBS 1% P/S | 144 |
| BT-474 | 1000 | ATCC HTB-20 | HYBRI-CARE (1 L $H_2O$, 1.5 g/L sodium bicarbonate, 10% FBS, 1% P/S) | 144 |
| ZR-75-30 | 1000 | ATCC CRL-1504 | RMPI 10% FBS 1% P/S | 240 |

Incubate the plates at 37° C. and 5% $CO_2$. The following day dose the cells with the test compound, Example 1B.

Prepare compounds as 10 mM DMSO stock solutions and use for a dose response study with top concentration starting at 10 or 1 µM, two compounds tested together at a fixed ratio, and then 1:3 serial dilutions serial dilution prepared as well as compounds alone for $IC_{50}$ determination with a starting concentration of 20 µM. Dose the cells with the addition of 5 µL from the serial dilution plate to the cell plate, producing a final DMSO concentration of 0.2% with a final test compound concentration dose range between 20 and 0.001 µM for single treatment or lower range for the combinations. For the maximum point use media containing 0.2% of DMSO and for the minimum point use staurosporine diluted at 2 µM final concentrations in the growth media containing 0.2% DMSO. After dosing with the test compound, incubate the cell plates at 37° C. and 5% $CO_2$. After two doubling times incubation with the compounds, remove the plates from the incubator and add cold EtOH 96% (65 µL) to each well. After 30 minutes, remove the media and add RNase (20 µL of 50 µg/mL) (Sigma) and 1:1000 propidium iodide dilution in PBS per well. Seal the plates and incubate 1 hour at room temperature (preserved from light). Scan the plates with ACUMEN EXPLORER™ [Laser-scanning fluorescence microplate cytometer manufactured by TTP LABTECH LTD]. As some cell lines grows forming aggregates, cell number as number of objects may not be able to be used as readout; so total area population (a designated range of peak intensity of FL-1 (PI)) or total intensity of PI are used to evaluate cell number.

In vitro combination data suggests synergy (as defined below) with combination of Example 1B with abemaciclib, or everolimus in 5 out of 5 ER-positive breast cancer cell lines as shown in Table 15. Combination of Example 1B with Compound A synergistic in 4 out of 4 ER-positive breast cancer cell lines tested. Combination effect of Example 1B with alpelisib is additive in 2 out of 4 ER-positive breast cancer cell lines and synergistic in 2 out of 4 ER-positive breast cancer cell lines.

TABLE 15

In vitro combination of Example 1B with other targeted agents in ER-positive breast cancer cell lines

| Breast cancer cell line | Treatment 1 | Treatment 2 | Combination Index (CI50) | Statistical Interpretation | Biological Interpretation |
|---|---|---|---|---|---|
| MCF7 | Example 1B | Abemaciclib | 0.2675 | Synergistic | Additive |
|  |  | Everolimus | 0.0389 | Synergistic | Synergistic |
| T47D | Example 1B | Abemaciclib | 0.2693 | Synergistic | Synergistic |
|  |  | Everolimus | 0.0609 | Synergistic | Synergistic |
|  |  | alpelisib | 0.0818 | Synergistic | Synergistic |
|  |  | Compound A | 0.2401 | Synergistic | Synergistic |
| ZR-75-1 | Example 1B | Abemaciclib | 0.2067 | Synergistic | Synergistic |
|  |  | Everolimus | 0.1853 | Synergistic | Synergistic |
|  |  | alpelisib | 1.3717 | Additive | Additive |
|  |  | Compound A | 0.3768 | Synergistic | Synergistic |
| ZR-75-30 | Example 1B | Abemaciclib | 0.3960 | Synergistic | Synergistic |
|  |  | Everolimus | 0.1248 | Synergistic | Synergistic |
|  |  | alpelisib | 0.4149 | Additive | Additive |
|  |  | Compound A | 0.7098 | Synergistic | Synergistic |
| EFM-19 | Example 1B | Abemaciclib | 0.3455 | Synergistic | Synergistic |
|  |  | Everolimus | 0.5033 | Synergistic | Additive |
|  |  | alpelisib | 0.2963 | Synergistic | Synergistic |
|  |  | Compound A | 0.4326 | Synergistic | Synergistic |

Data Analysis and Interpretation of Combination Effect

Use methods that are published in the literature to calculate in vitro combination effect (L. Zhao, et al, Front Biosci, 2010, 2:241-249 and L. Zhao, et al, Clin Cancer Res, 2004, 10(23):7994-8004). In order to identify synergistic or antagonistic interactions between two drugs, a curve shift analysis has been performed using a customized XL template with XLFit 5 add ins. Single agent's curves are adjusted using 4 parameters logistic regression. Criteria and restrictions used for the fitting are (i) bottoms <(−20) are fixed to 0 and (ii) top >120 fixed to 100. If all the observations are lower than a threshold set by the user, then a constant fit with hill=0 is performed and the $IC_{50}$ is considered higher than the maximum included concentration. Once the absolute $IC_{50}$ of each single agent has been obtained, the equivalent concentration at 50% of activity is calculated for the singles and combination. Using these equivalent concentrations together with the measured activities we recalculate an absolute $IC_{50}$, the curve for single agents will reach 50% activity at values of eq concentrations equals to 1, while synergistic combinations will reach the 50% at lower values resulting in a leftward shift, and antagonistic combination will show rightward shift. Equivalent concentrations are also used to calculate $CI_{50}$ (Combination Index at 50% of activity), where $CI_{50}$ equals absolute $IC_{50}$ of combination curve. Together with $CI_{50}$ other CI's (Combination Indexes) at different percentages of activity can be calculated ($CI_{10}$, $CI_{20}$, $CI_{30}$, $CI_{40}$, $CI_{60}$, $CI_{70}$, $CI_{80}$, $CI_{90}$). In order to calculate CInn, equivalent concentration at different activity percentage are calculated. For each activity percentage we calculate the margin of error which is the confidence interval at 95% and using this confidence interval we will calculate upper limit as the addition of margin of error to the CI and the lower limit as the subtraction of the margin of error to the CI. Upper limit=CI+Confidence interval 95% and Lower Limit=CI-Confidence interval 95%. These limits are then used to interpret the results.

Statistical Interpretation at each activity percentage is as follows:

| | |
|---|---|
| Lower limit <1 and upper limit >1 | Additive |
| Upper limit <1 | Synergy |
| Lower limit >1 | Antagonist |

Biological Interpretation at each activity percentage is as follows:

| | |
|---|---|
| CInn <0.5 | Synergy |
| CInn >0.5 and CInn <2 | Additive |
| CInn >2 | Antagonist |

In Vivo Combination Studies

Due to tumor heterogeneity and acquired resistance to endocrine therapies, combination therapy has become essential in ER-positive and advanced/metastatic breast cancer treatment for effective therapy or to overcome acquired resistance. It is hypothesized that a combination of targeted therapies has the potential to be more effective in slowing or even halting ER-positive breast cancers. Combination of CDK4/6 inhibitors and fulvestrant has been approved for the treatment of ER-positive metastatic breast cancer but a high percentage of patients develop resistance due to acquired mutations in ESR1 or PIK3CA. As a potent degrader and antagonist of ERα, oral SERD such as Example 1B has the potential to be more effective in slowing or halting ESR1 mutant or PIK3CA mutant breast cancers as a single agent or in combination with CDK4/6 inhibitor such as abemaciclib or PI3K/mTOR inhibitor such as Compound A. In that context, the compound of Example 1B is tested for tumor growth inhibition in combination with abemaciclib (patent reference) or Compound A (patent reference). More specifically the compound of Example 1B is tested in combination with abemaciclib or Compound A in ESR1 wild type and PIK3Ca mutant MCF7 breast cancer xenograft model.

Expand human breast cancer cells MCF7 (ATCC #HTB-22) in culture, harvest and inject $5 \times 10e^6$ cells in 1:1 HBSS+MATRIGEL™ solution (200 µL) subcutaneously on to the rear right flank of female NOD SCID mice (22-25 g, Envigo RMS, Inc). Twenty-four hours prior to implantation of cells, implant estrogen pellets (0.18 mg/pellet, 17β estradiol, 90-day release, Innovative Research) subcutaneously. Measure tumor growth and body weight twice per week beginning the seventh day after the implantation. When tumor sizes reach 250-350 mm$^3$, randomize animals and group into groups of 5 animals. Prepare the test compound Example 1B in an appropriate vehicle (1% hydroxyethylcellulose/0.25% TWEEN® 80/0.05% Antifoam in purified water) and administer by oral gavage for 42 days. The CDK4/6 inhibitor (abemaciclib) is formulated in 1% HEC in 25 mM sodium phosphate buffer, pH 2.0. The PI3K/mTOR inhibitor (Compound A) was formulated in 1% hydroxyethylcellulose/0.25% TWEEN® 80/0.05% Antifoam in purified water. Determine tumor response by tumor volume measurement performed twice a week during the course of treatment. Take the body weight as a general measure of toxicity whenever tumor volume is measured. Tumor volume is estimated by using the formula $v = l \times w2 \times 0.535$ where l=larger of measured diameter and w=smaller of perpendicular diameter.

Statistical Analysis

The statistical analysis of the tumor volume data begins with a data transformation to a log scale to equalize variance across time and treatment groups. The log volume data are analyzed with a two-way repeated measures analysis of variance by time and treatment using the MIXED procedures in SAS software (Version 9.3). The correlation model for the repeated measures is Spatial Power. Treated groups are compared to the control group at each time point. The MIXED procedure is also used separately for each treatment group to calculate adjusted means and standard errors at each time point. Both analyses account for the autocorrelation within each animal and the loss of data that occurs when animals with large tumors are removed from the study early. The adjusted means and standard errors (s.e.) are plotted for each treatment group versus time. Analysis for tumor volume is based on $\log_{10}$ and spatial power covariance structure. P value is based on the comparison between two specific groups.

Combination Analysis Method (Bliss Independence for IVEF Studies)

First, the usual repeated measures model is fit to log volume versus group and time. Then contrast statements are used to test for an interaction effect at each time point using the 2 specific treatments that are combined. This is equivalent to the Bliss Independence method and assumes that tumor volumes can, in theory, reach zero, i.e., complete regression. The expected additive response (EAR) for the combination is calculated on the tumor volume scale as: response (EAR) EAR volume=V1*V2/V0, where V0, V1, and V2 are the estimated mean tumor volumes for the vehicle control, treatment 1 alone, and treatment 2 alone, respectively. If the interaction test is significant, the combination effect is declared statistically more than additive or less than additive depending on the observed combination mean volume being less than or more than the EAR volume, respectively. Otherwise, the statistical conclusion is additive. In addition, a biologically relevant range of additivity can be defined as X % above and below the EAR volume. Typically, X would be 25 to 40%. Then a biological conclusion can be made for the combination as more than additive, additive, or less than additive if the observed combination mean volume is below, in, or above the interval of additivity.

There may be situations were stasis is the best expected response. In those situations, the Bliss method can be applied directly to the % delta T/C values to obtain an EAR percent response: EAR % delta T/C=Y1*Y2/100, where Y1 and Y2 are the percent delta T/C values for the single-agent treatments. Currently, there is no statistical test to compare the observed % delta T/C in the combination group versus the EAR, but the biological criterion described above can be applied.

As shown in Table 15 and 16, treatment with Example 1B or abemaciclib alone as a single agent resulted in 32% (% dT/C=−32) and 52% (% dT/C=−52) tumor regressions respectively and both are statistically significant (p<0.001) compared to vehicle control. Combination efficacy of Example 1B with abemaciclib was "Less Than Additive" but the combination efficacy of Example 1B plus abemaciclib was significantly better than Example 1B alone (p<0.001). However, single agent abemaciclib efficacy was not statistically significant from combination (P=0.055). The combination is tolerated in the animals without significant body weight loss.

TABLE 15

Combination Efficacy of Example 1B with abemaciclib in MCF7 ER-positive breast cancer model

| Treatment 1 | Treatment 2 | Difference[b] | SE | p-value |
|---|---|---|---|---|
| Vehicle, QD × 42, PO | Example 1B, 10 mpk, QD × 42, PO | 0.628 | 0.0658 | <0.001* |
| Vehicle, QD × 42, PO | Abemaciclib, 50 mpk, QD × 42, PO | 0.479 | 0.0658 | <0.001* |
| Vehicle, QD × 42, PO | Example 1B, 10 mpk, QD × 42, PO/ Abemaciclib, 50 mpk, QD × 42, PO | 0.756 | 0.0658 | <0.001* |
| Example 1B, 10 mpk, QD × 42, PO | Example 1B, 10 mpk, QD × 42, PO/ Abemaciclib, 50 mpk, QD × 42, PO | 0.128 | 0.0658 | 0.055 |
| Abemaciclib, 50 mpk, QD × 42, PO | Example 1B, 10 mpk, QD × 42, PO/ Abemaciclib, 50 mpk, QD × 42, PO PO | 0.278 | 0.0658 | <0.001* |

[b]Difference = Treatment 1 − Treatment 2;
*p-value: significant (p < 0.05)
SE-Standard error

TABLE 16

Combination Efficacy of Example 1B with abemaciclib in MCF7 ER-positive breast cancer model

| Treatment | Delta T/C % or % Regression | p-value | Combination Effect | Bodyweight |
|---|---|---|---|---|
| Vehicle | NA | NA | | |
| Example 1B | −32 | <0.001* | | |
| Abemaciclib | −52 | <0.001* | | |
| Example 1B/ Abemaciclib/ (Combination) | −64 | <0.001* | Less Than Additive | No significant change |

Analysis for tumor volume is based on $Log_{10}$ and Spatial Power covariance structure.
*p-value: significant (p<0.05); NA: Not applicable
Delta T/C % is calculated when the endpoint tumor volume in a treated group is at or above baseline tumor volume; and regression % is calculated for tumor volume below the baseline. The formula is $100*(T-T_0)/(C-C_0)$, where T and C are mean endpoint tumor volumes in the treated or control group, respectively. $T_0$ and $C_0$ are mean baseline tumor volumes in those groups.

As shown in Tables 17 and 18, treatment with Example 1B or Compound A alone as a single agent resulted in 32% (% dT/C=−32) and 36% (% dT/C=−36) tumor regressions respectively and both are statistically significant (p<0.001) compared to vehicle control. Combination efficacy of Example 1B with Compound A was "Less Than Additive" but the combination efficacy of Example 1B plus Compound A was significantly better than Example 1B alone (p<0.001) or Compound A alone (p=0.002*). The combination is tolerated in the animals without significant body weight loss.

TABLE 17

Combination Efficacy of Example 1B with Compound A in MCF7 ER-positive breast cancer model

| Treatment 1 | Treatment 2 | Difference[b] | SE | p-value |
|---|---|---|---|---|
| Vehicle, QD × 42, PO | Example 1B, 10 mpk, QD × 42, PO | 0.479 | 0.0759 | <0.001* |
| Vehicle, QD × 42, PO | Compound A, 7.5 mpk, BID × 42, PO | 0.504 | 0.0759 | <0.001* |
| Vehicle, QD × 42, PO | Example 1B, 10 mpk, QD × 42, PO/Compound A, 7.5 mpk, BID × 42, PO | 0.761 | 0.0791 | <0.001* |
| Example 1B, 10 mpk, QD × 42, PO | Example 1B, 10 mpk, QD × 42, PO/Compound A, 7.5 mpk, BID × 42, PO | 0.282 | 0.0791 | <0.001* |
| Compound A, 7.5 mpk, BID × 42, PO | Example 1B, 10 mpk, QD × 42, PO/Compound A, 7.5 mpk, BID × 42, PO PO | 0.257 | 0.0791 | 0.002* |

[b]Difference = Treatment 1 − Treatment 2;
*p-value: significant (p < 0.05)
SE-Standard error

TABLE 18

Combination Efficacy of Example 1B with abemaciclib in MCF7 ER-positive breast cancer model

| Treatment | Delta T/C % or % Regression | p-value | Combination Effect | Bodyweight |
|---|---|---|---|---|
| Vehicle | NA | NA | | |
| Example 1B | −32 | <0.001* | | |
| Compound A | −36 | <0.001* | | |
| Example 1B/ Compound A/ (Combination) | −65 | <0.001* | Less Than Additive | No significant change |

Analysis for tumor volume is based on $Log_{10}$ and Spatial Power covariance structure.
*p-value: significant (p<0.05); NA: Not applicable
Delta T/C % is calculated when the endpoint tumor volume in a treated group is at or above baseline tumor volume; and regression % is calculated for tumor volume below the baseline. The formula is $100*(T-T_0)/(C-C_0)$, where T and C are mean endpoint tumor volumes in the treated or control group, respectively. $T_0$ and $C_0$ are mean baseline tumor volumes in those groups.

As shown in Tables 19 and 20, treatment with Example 10 or abemaciclib alone as a single agent resulted in 51% (% dT/C=−51) and 70% (% dT/C=−70) tumor regressions respectively and both are statistically significant (p<0.001) compared to vehicle control. Combination efficacy of Example 10 with abemaciclib was "Less Than Additive" but the combination efficacy of Example 10 plus abemaciclib was significantly better than Example 10 alone (p=0.039). However, combination efficacy of Example 10 plus abemaciclib was not significantly different from abemaciclib alone (p=0.905). The combination is tolerated in the animals without significant body weight loss.

TABLE 19

Combination Efficacy of Example 10 with abemaciclib in MCF7 ER-positive breast cancer model

| Treatment 1 | Treatment 2 | Difference[b] | SE | p-value |
|---|---|---|---|---|
| Vehicle, QD × 42, PO | Example 10, 15 mpk, QD × 42, PO | 0.659 | 0.113 | <0.001* |
| Vehicle, QD × 42, PO | Abemaciclib 50 mpk, QD × 42, PO | 0.445 | 0.1054 | <0.001* |
| Vehicle, QD × 42, PO | Example 10, 15 mpk, QD × 42, PO/abemaciclib, 50 mpk, QD × 42, PO | 0.672 | 0.1054 | <0.001* |
| Example 10, 15 mpk, QD × 42, PO | Example 10, 15 mpk, QD × 42, PO/abemaciclib, 50 mpk, QD × 42, PO | 0.013 | 0.1103 | 0.905 |
| Abemaciclib, 50 mpk, QD × 42, PO | Example 10, 15 mpk, QD × 42, PO/abemaciclib, 50 mpk, QD × 42, PO PO | 0.227 | 0.1054 | 0.039* |

[b]Difference = Treatment 1 − Treatment 2;
*p-value: significant (p < 0.05)
SE-Standard error

TABLE 20

Combination Efficacy of Example 10 with abemaciclib in MCF7 ER-positive breast cancer model

| Treatment | Delta T/C % or % Regression | p-value | Combination Effect | Bodyweight |
|---|---|---|---|---|
| Vehicle | NA | NA | | |
| Example 10 | −51 | <0.001* | | |
| Abemaciclib | −70 | <0.001* | | |
| Example 10/ Abemaciclib/ (Combination) | −71 | <0.001* | Less Than Additive | No significant change |

Analysis for tumor volume is based on $Log_{10}$ and Spatial Power covariance structure.
*p-value: significant (p<0.05); NA: Not applicable
Delta T/C % is calculated when the endpoint tumor volume in a treated group is at or above baseline tumor volume; and regression % is calculated for tumor volume below the baseline. The formula is $100*(T-T_0)/(C-C_0)$, where T and C are mean endpoint tumor volumes in the treated or control group, respectively. $T_0$ and $C_0$ are mean baseline tumor volumes in those groups.

As shown in Table 21 and 22, treatment with Example 10 or alpelisib alone as a single agent resulted in 51% (% dT/C=−51) and 21% (% dT/C=−21) tumor regressions respectively and both are statistically significant (p<0.001 and p=0.013) compared to vehicle control. Combination efficacy of Example 10 with alpelisib was "Additive" and the combination efficacy of Example 10 plus alpelisib was significantly better than Example 10 alone (p=0.009). Combination efficacy of Example 10 plus alpelisib was also significantly better than alpelisib alone (p=<0.001). The combination is tolerated in the animals without significant body weight loss.

TABLE 21

Combination Efficacy of Example 10 with alpelisib in MCF7 ER-positive breast cancer model

| Treatment 1 | Treatment 2 | Difference[b] | SE | p-value |
|---|---|---|---|---|
| Vehicle, QD × 42, PO | Example 10, 15 mpk, QD × 42, PO | 0.241 | 0.1121 | <0.039* |
| Vehicle, QD × 42, PO | alpelisib 15 mpk (d1-d7,), 10 mpk (d8-42), mpk, QD × 42, PO | 0.445 | 0.1121 | <0.001* |
| Vehicle, QD × 42, PO | Example 10, 15 mpk, QD × 42, PO/alpelisib 15 mpk (d1-d7,), 10 mpk (d8-42), mpk, QD × 42, PO | 0.755 | 0.1121 | <0.001* |
| Example 10, 15 mpk, QD × 42, PO | Example 10, 15 mpk, QD × 42, PO/alpelisib 15 mpk (d1-d7,), 10 mpk (d8-42), mpk, QD × 42, PO | 0.514 | 0.1121 | <0.001 |
| alpelisib 15 mpk (d1-d7,), 10 mpk (d8-42), mpk, QD × 42, PO | Example 10, 15 mpk, QD × 42, PO/alpelisib 15 mpk (d1-d7,), 10 mpk (d8-42), mpk, QD × 42, PO | 0.310 | 0.1121 | 0.009* |

[b]Difference = Treatment 1 − Treatment 2;
*p-value: significant (p < 0.05)
SE-Standard error

TABLE 22

Combination Efficacy of Example 10 with alpelisib in MCF7 ER-positive breast cancer model

| Treatment | Delta T/C % or % Regression | p-value | Combination Effect | Bodyweight |
|---|---|---|---|---|
| Vehicle | NA | NA | | |
| Example | 10 −51 | <0.001* | | |
| alpelisib | −21 | <0.013* | | |
| Example 10/ alpelisib (Combination) | −76 | <0.001* | Additive | No significant change |

Analysis for tumor volume is based on $Log_{10}$ and Spatial Power covariance structure.
*p-value: significant (p<0.05); NA: Not applicable
Delta T/C % is calculated when the endpoint tumor volume in a treated group is at or above baseline tumor volume; and regression % is calculated for tumor volume below the baseline. The formula is $100*(T-T_0)/(C-C_0)$, where T and C are mean endpoint tumor volumes in the treated or control group, respectively. $T_0$ and $C_0$ are mean baseline tumor volumes in those groups.

As shown in Table 23 and 24, treatment with Example 10 or everolimus alone as a single agent resulted in 51% (% dT/C=−51) and 50% (% dT/C=−50) tumor regressions respectively and both are statistically significant (p<0.001 and p<0.001) compared to vehicle control. Combination efficacy of Example 10 with everolimus was "Additive" and the combination efficacy of Example 10 plus everolimuswas significantly better than Example 10 alone (p=0.004). Combination efficacy of Example 10 plus alpelisib was also significantly better than everolimus alone (p=0.04). The combination is tolerated in the animals without significant body weight loss.

TABLE 23

Combination Efficacy of Example 10 with everolimus in MCF7 ER-positive breast cancer model

| Treatment 1 | Treatment 2 | Difference[b] | SE | p-value |
|---|---|---|---|---|
| Vehicle, QD × 42, PO | Example 10, 15 mpk, QD × 42, PO | 0.445 | 0.0999 | <0.001* |
| Vehicle, QD × 42, PO | Everolimus, 5 mpk, QD × 42, PO | 0.433 | 0.1038 | <0.001* |
| Vehicle, QD × 42, PO | Example 10, 15 mpk, QD × 42, PO/Everolimus, 5 mpk, QD × 42, PO | 0.748 | 0.0999 | <0.001* |
| Example 10, 15 mpk, QD × 42, PO | Example 10, 15 mpk, QD × 42, PO/Everolimus, 5 mpk, QD × 42, PO | 0.303 | 0.0999 | 0.004* |
| Everolimus, 5 mpk, QD × 42, PO | Example 10, 15 mpk, QD × 42, PO/Everolimus, 5 mpk, QD × 42, PO | 0.315 | 0.138 | 0.004* |

[b]Difference = Treatment 1 − Treatment 2;
*p-value: significant (p < 0.05)
SE-Standard error

TABLE 24

Combination Efficacy of Example 10 with everolimus in MCF7 ER-positive breast cancer model

| Treatment | Delta T/C % or % Regression | p-value | Combination Effect | Bodyweight |
|---|---|---|---|---|
| Vehicle | NA | NA | | |
| Example 10 | −51 | <0.001* | | |
| Everolimus | −50 | <0.001* | | |
| Example 10/ Everolimus (Combination) | −76 | <0.001* | Additive | No significant change |

Analysis for tumor volume is based on $Log_{10}$ and Spatial Power covariance structure.
*p-value: significant (p<0.05); NA: Not applicable
Delta T/C % is calculated when the endpoint tumor volume in a treated group is at or above baseline tumor volume; and regression % is calculated for tumor volume below the baseline. The formula is $100*(T-T_0)/(C-C_0)$, where T and C are mean endpoint tumor volumes in the treated or control group, respectively. $T_0$ and $C_0$ are mean baseline tumor volumes in those groups.

Rat Oral Bioavailability Assay

The purpose of the following assay is to demonstrate whether a test compound is orally bioavailable.

Administer the test compound to Sprague-Dawley rats IV at 1 mg/kg (using vehicles of either: 20% CAPTISOL® in 25 mM sodium phosphate buffer, pH2 quantum satis; or 25% DMA, 15% EtOH, 10% propylene glycol, 25% 2-pyrrolidone, and 25% purified water) and PO at 10 mg/kg (using a vehicle of 1% hydroxyethyl cellulose, 0.25% polysorbate 80, 0.05% Antifoam 1510-US, and purified water quantum satis). Collect serial blood samples at 0.08, 0.25, 0.5, 1, 2, 4, 8, and 12 hours post dose for IV bolus and at 0.25, 0.5, 1, 2, 4, 8, and 12 hours post dose after oral administration. After treatment with an EDTA coagulant, obtain plasma by centrifugation and store at −70° C. until analysis by LC-MS/MS. Determine the test compound concentration in plasma and upload into the Watson LIMS™ system where noncompartmental analysis is used to calculate Area Under the Curve (AUC) for both IV and PO arms. Calculate oral bioavailability (% F) via the following equation, $$\% F=(AUC_{PO} \times Dose_{IV})/(AUC_{IV} \times Dose_{PO}) \times 100.$$

The compounds of Example 1B displays a % F value of ~50% in the above-mentioned assay. This assay demonstrates that Example 1B has good oral bioavailability.

We claim:

1. A crystalline form of the compound of the formula:

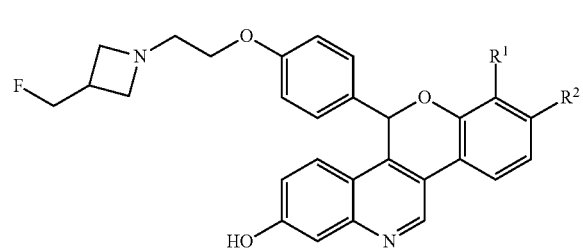

wherein either $R^1$ or $R^2$ is independently selected from Cl, F, —$CF_3$, or —$CH_3$, and the other is hydrogen, or a pharmaceutically acceptable salt thereof.

2. A crystalline form according to claim 1, wherein the compound is

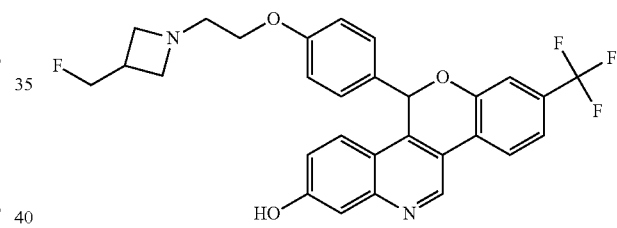

pharmaceutically acceptable salt thereof.

3. A crystalline form according to claim 2, characterized by having an X-ray powder diffraction (XRPD) pattern comprising peaks at ° 2θ values of 19.8±0.2, in combination with one or more of the peaks selected from the group consisting of 6.8±0.2, 16.0±0.2, and 22.1±0.2.

4. A crystalline form according to claim 2, characterized by having an X-ray powder diffraction (XRPD) pattern comprising peaks at ° 2θ values of

| Peak | Angle (°2-Theta) +/− 0.2° | Relative Intensity (% of most intense peak) |
|---|---|---|
| 1 | 6.8 | 29.40 |
| 2 | 15.3 | 8.30 |
| 3 | 16.0 | 20.10 |
| 4 | 17.4 | 7.60 |
| 5 | 18.1 | 16.00 |
| 6 | 19.8 | 100.00 |
| 7 | 21.1 | 14.60 |
| 8 | 22.1 | 28.90 |
| 9 | 24.9 | 16.40 |
| 10 | 25.4 | 21.90. |

5. A crystalline form according to claim 2, wherein the pharmaceutically acceptable salt is a benzenesulfonic acid salt.

6. A crystalline form according to claim 5, characterized by having an X-ray powder diffraction (XRPD) pattern comprising peaks at ° 2θ values of wherein the compound is 20.5±0.2 in combination with one or more of the peaks selected from the group consisting of 12.3±0.2, 22.2±0.2, and 23.1±0.2.

7. A crystalline form according to claim 5, characterized by having an X-ray powder diffraction (XRPD) pattern comprising peaks at ° 2θ values of

| Peak | Angle (°2-Theta) +/− 0.2° | Relative Intensity (% of most intense peak) |
| --- | --- | --- |
| 1 | 7.6 | 27.10 |
| 2 | 10.6 | 34.50 |
| 3 | 12.3 | 42.10 |
| 4 | 12.6 | 32.30 |
| 5 | 17.7 | 32.80 |
| 6 | 19.2 | 26.70 |
| 7 | 20.5 | 100.00 |
| 8 | 22.2 | 45.50 |
| 9 | 23.1 | 36.30 |
| 10 | 24.2 | 29.80. |

8. A crystalline form according to claim 2, wherein the pharmaceutically acceptable salt is a 4-methylbenzenesulfonic acid salt.

9. A crystalline form according to claim 8, characterized by having an X-ray powder diffraction (XRPD) pattern comprising peaks at ° 2θ values of wherein the compound is 20.1±0.2 in combination with one or more of the peaks selected from the group consisting of 12.8±0.2, 19.5±0.2, and 22.8±0.2.

10. A crystalline form according to claim 8, characterized by having an X-ray powder diffraction (XRPD) pattern comprising peaks at ° 2θ values of

| Peak | Angle (°2-Theta) +/− 0.2° | Relative Intensity (% of most intense peak) |
| --- | --- | --- |
| 1 | 7.6 | 25.70 |
| 2 | 12.4 | 27.90 |
| 3 | 12.8 | 36.80 |
| 4 | 18.9 | 26.50 |
| 5 | 19.5 | 56.90 |
| 6 | 20.1 | 100.00 |
| 7 | 20.9 | 41.50 |
| 8 | 21.8 | 40.90 |
| 9 | 22.8 | 39.40 |
| 10 | 25.4 | 29.70. |

11. A pharmaceutical composition comprising the compound or the pharmaceutically acceptable salt thereof according to claim 1 in combination with a pharmaceutically acceptable excipient, carrier, or diluent.

12. The pharmaceutical composition according to claim 11, comprising one or more other therapeutic agents.

13. A method of treating breast cancer, ovarian cancer, endometrial cancer, prostate cancer, uterine cancer, gastric cancer, or lung cancer, comprising administering to a patient in need of such treatment an effective amount of a compound or a pharmaceutically acceptable salt thereof according to claim 1.

14. The method according to claim 13, wherein the breast cancer is ER-positive breast cancer.

15. The method according to claim 13, wherein the gastric cancer is ER-positive gastric cancer.

16. The method according to claim 13, wherein the lung cancer is ER-positive lung cancer.

* * * * *